US008882756B2

(12) United States Patent
Greeley et al.

(10) Patent No.: US 8,882,756 B2
(45) Date of Patent: Nov. 11, 2014

(54) FLUID-ASSISTED ELECTROSURGICAL DEVICES, METHODS AND SYSTEMS

(75) Inventors: Roger D. Greeley, Portsmouth, NH (US); Steven G. Miller, Milton, NH (US); Vaclav O. Podany, New Fairfield, CT (US); Brian M. Conley, South Berwick, ME (US); Chad M. Greenlaw, Somersworth, NH (US)

(73) Assignee: Medtronic Advanced Energy LLC, Minneapolis, MN (US)

( * ) Notice: Subject to any disclaimer, the term of this patent is extended or adjusted under 35 U.S.C. 154(b) by 1174 days.

(21) Appl. No.: 12/343,744

(22) Filed: Dec. 24, 2008

(65) Prior Publication Data
US 2009/0222001 A1    Sep. 3, 2009

Related U.S. Application Data

(60) Provisional application No. 61/017,403, filed on Dec. 28, 2007.

(51) Int. Cl.
*A61B 18/04* (2006.01)
*A61B 19/00* (2006.01)
*A61B 18/12* (2006.01)
*A61B 18/00* (2006.01)
*A61B 18/14* (2006.01)

(52) U.S. Cl.
CPC ....... *A61B 18/1402* (2013.01); *A61B 2019/521* (2013.01); *A61B 2018/126* (2013.01); *A61B 2018/00136* (2013.01); *A61B 2018/1472* (2013.01); *A61B 2218/002* (2013.01); *A61B 2019/5206* (2013.01)
USPC ............................... 606/32; 604/22; 604/507

(58) Field of Classification Search
USPC ........................... 606/31, 41, 32; 604/22, 507
See application file for complete search history.

(56) References Cited

U.S. PATENT DOCUMENTS

| | | | |
|---|---|---|---|
| 2,888,928 | A | 6/1959 | Seiger |
| 3,682,130 | A | 8/1972 | Jeffers |
| 3,750,650 | A | 8/1973 | Ruttgers |
| 4,060,088 | A | 11/1977 | Morrison, Jr. et al. |
| 4,207,897 | A | 6/1980 | Lloyd et al. |

(Continued)

FOREIGN PATENT DOCUMENTS

WO    WO 98 27879    7/1998

OTHER PUBLICATIONS

European Office Action dated May 6, 2009 issued in related European Patent Application No. 05851938.0.

(Continued)

*Primary Examiner* — Nicholas Lucchesi
*Assistant Examiner* — Scott Medway
(74) *Attorney, Agent, or Firm* — Jeffrey J. Hohenshell

(57) ABSTRACT

The invention provides a bipolar electrosurgical device to treat tissue in a presence of radio frequency energy and a fluid provided from the device. In one embodiment, the device comprises a first electrode and a second electrode at the end of a malleable shaft assembly to be hand shapeable by a user of the device, and at least one fluid outlet. The malleable shaft assembly comprises a first shaft and a second shaft, a length of the first shaft and a length of the second shaft in an outer member comprising a polymer, and at least a portion of the first shaft and at least a portion of the second shaft being malleable.

28 Claims, 15 Drawing Sheets

(56) References Cited

U.S. PATENT DOCUMENTS

| | | | |
|---|---|---|---|
| 4,244,371 A | 1/1981 | Farin |
| 4,248,224 A | 2/1981 | Jones |
| 4,275,734 A | 6/1981 | Mitchiner |
| 4,276,874 A | 7/1981 | Wolvek et al. |
| 4,278,090 A | 7/1981 | van Gerven |
| 4,321,931 A | 3/1982 | Hon |
| 4,342,218 A | 8/1982 | Fox |
| 4,355,642 A | 10/1982 | Alferness |
| 4,377,168 A | 3/1983 | Rzasa et al. |
| 4,381,007 A | 4/1983 | Doss |
| 4,519,389 A | 5/1985 | Gudkin et al. |
| 4,598,698 A | 7/1986 | Siegmund |
| 4,601,290 A | 7/1986 | Effron et al. |
| 4,664,110 A | 5/1987 | Schanzlin |
| 4,671,274 A | 6/1987 | Scrochenko |
| 4,736,749 A | 4/1988 | Lundback |
| 4,742,819 A * | 5/1988 | George | 600/109 |
| 4,779,611 A | 10/1988 | Grooters et al. |
| 4,802,475 A | 2/1989 | Weshahy |
| 4,815,470 A | 3/1989 | Curtis et al. |
| 4,872,346 A | 10/1989 | Kelly-Fry et al. |
| 4,916,922 A | 4/1990 | Mullens |
| 4,917,095 A | 4/1990 | Fry et al. |
| 4,919,129 A | 4/1990 | Weber et al. |
| 4,931,047 A | 6/1990 | Broadwin et al. |
| 4,932,952 A | 6/1990 | Wojciechowicz, Jr. |
| 4,936,281 A | 6/1990 | Stasz |
| 4,943,290 A | 7/1990 | Rexroth et al. |
| 4,946,460 A | 8/1990 | Merry et al. |
| 4,950,232 A | 8/1990 | Ruzicka et al. |
| 4,985,030 A | 1/1991 | Melzer et al. |
| 4,998,933 A | 3/1991 | Eggers et al. |
| 5,013,312 A | 5/1991 | Parins et al. |
| 5,029,574 A | 7/1991 | Shimamura et al. |
| 5,044,165 A | 9/1991 | Linner et al. |
| 5,078,713 A | 1/1992 | Varney |
| 5,080,102 A | 1/1992 | Dory |
| 5,080,660 A | 1/1992 | Buelina |
| 5,100,388 A | 3/1992 | Behl et al. |
| 5,108,390 A | 4/1992 | Potocky et al. |
| 5,147,355 A | 9/1992 | Freidman et al. |
| 5,160,194 A * | 11/1992 | Feldman | 362/109 |
| 5,178,133 A | 1/1993 | Pena |
| 5,190,541 A | 3/1993 | Abele et al. |
| 5,195,959 A | 3/1993 | Smith |
| 5,207,674 A | 5/1993 | Hamilton |
| 5,217,860 A | 6/1993 | Fahy et al. |
| 5,222,501 A | 6/1993 | Ideker et al. |
| 5,224,943 A | 7/1993 | Goddard |
| 5,228,923 A | 7/1993 | Hed |
| 5,231,995 A | 8/1993 | Desai |
| 5,232,516 A | 8/1993 | Hed |
| 5,234,428 A | 8/1993 | Kaufman |
| 5,250,047 A | 10/1993 | Rydell |
| 5,254,116 A | 10/1993 | Baust et al. |
| 5,254,117 A | 10/1993 | Rigby et al. |
| 5,263,493 A | 11/1993 | Avitall |
| 5,269,291 A | 12/1993 | Carter |
| 5,275,595 A | 1/1994 | Dobak, III |
| 5,277,201 A | 1/1994 | Stern |
| 5,281,213 A | 1/1994 | Milder et al. |
| 5,281,215 A | 1/1994 | Milder |
| 5,295,484 A | 3/1994 | Marcus et al. |
| 5,309,896 A | 5/1994 | Moll et al. |
| 5,316,000 A | 5/1994 | Chapelon et al. |
| 5,317,878 A | 6/1994 | Bradshaw et al. |
| 5,318,525 A | 6/1994 | West et al. |
| 5,322,520 A | 6/1994 | Milder |
| 5,323,781 A | 6/1994 | Ideker et al. |
| 5,324,255 A | 6/1994 | Passafaro et al. |
| 5,324,284 A | 6/1994 | Imran |
| 5,324,286 A | 6/1994 | Fowler |
| 5,330,521 A | 7/1994 | Cohen |
| 5,334,181 A | 8/1994 | Rubinsky et al. |
| 5,334,193 A | 8/1994 | Nardella |
| 5,336,220 A | 8/1994 | Ryan et al. |
| 5,348,554 A | 9/1994 | Imran et al. |
| 5,353,783 A | 10/1994 | Nakao et al. |
| 5,354,258 A | 10/1994 | Dory |
| 5,361,752 A | 11/1994 | Moll et al. |
| 5,383,874 A | 1/1995 | Jackson et al. |
| 5,385,148 A | 1/1995 | Lesh et al. |
| 5,395,312 A | 3/1995 | Desai |
| 5,396,887 A | 3/1995 | Imran |
| 5,397,304 A | 3/1995 | Truckai |
| 5,400,770 A | 3/1995 | Nakao et al. |
| 5,400,783 A | 3/1995 | Pomeranz et al. |
| 5,401,272 A | 3/1995 | Perkins |
| 5,403,309 A | 4/1995 | Coleman et al. |
| 5,403,311 A | 4/1995 | Abele et al. |
| 5,405,376 A | 4/1995 | Mulier et al. |
| 5,409,483 A | 4/1995 | Campbell et al. |
| 5,417,709 A | 5/1995 | Slater |
| 5,423,807 A | 6/1995 | Mlilder |
| 5,423,811 A | 6/1995 | Imran et al. |
| 5,427,119 A | 6/1995 | Swartz et al. |
| 5,431,168 A | 7/1995 | Webster, Jr. |
| 5,431,649 A | 7/1995 | Mulier et al. |
| 5,433,708 A | 7/1995 | Nichols et al. |
| 5,435,308 A | 7/1995 | Gallup et al. |
| 5,437,651 A | 8/1995 | Todd et al. |
| 5,441,503 A | 8/1995 | Considine et al. |
| 5,443,463 A | 8/1995 | Stern et al. |
| 5,443,470 A | 8/1995 | Stern et al. |
| 5,445,638 A | 8/1995 | Rydell et al. |
| 5,450,843 A | 9/1995 | Moll et al. |
| 5,452,582 A | 9/1995 | Longsworth |
| 5,452,733 A | 9/1995 | Sterman et al. |
| 5,460,629 A | 10/1995 | Shlain et al. |
| 5,462,545 A | 10/1995 | Wang et al. |
| 5,465,717 A | 11/1995 | Imran et al. |
| 5,469,853 A | 11/1995 | Law et al. |
| 5,472,876 A | 12/1995 | Fahy |
| 5,478,309 A | 12/1995 | Sweezer et al. |
| 5,478,330 A | 12/1995 | Imran et al. |
| 5,486,193 A | 1/1996 | Bourne et al. |
| 5,487,385 A | 1/1996 | Avitall |
| 5,487,757 A | 1/1996 | Truckai et al. |
| 5,490,819 A | 2/1996 | Nicholas et al. |
| 5,496,312 A | 3/1996 | Klicek |
| 5,497,774 A | 3/1996 | Swartz et al. |
| 5,498,248 A | 3/1996 | Milder |
| 5,500,012 A | 3/1996 | Brucker et al. |
| 5,505,730 A | 4/1996 | Edwards |
| 5,516,505 A | 5/1996 | McDow |
| 5,520,682 A | 5/1996 | Baust et al. |
| 5,522,870 A | 6/1996 | Ben-Zion |
| 5,536,267 A | 7/1996 | Edwards et al. |
| 5,540,562 A | 7/1996 | Giter |
| 5,542,916 A | 8/1996 | Hirsch et al. |
| 5,542,945 A | 8/1996 | Fritzsch |
| 5,545,195 A | 8/1996 | Lennox et al. |
| 5,545,200 A | 8/1996 | West et al. |
| 5,549,661 A | 8/1996 | Kordis et al. |
| 5,555,883 A | 9/1996 | Avitall |
| 5,556,397 A | 9/1996 | Long et al. |
| 5,558,671 A | 9/1996 | Yates |
| 5,560,362 A | 10/1996 | Silwa, Jr. et al. |
| 5,562,702 A | 10/1996 | Huitema et al. |
| 5,562,720 A | 10/1996 | Stern et al. |
| 5,569,241 A | 10/1996 | Edwards |
| 5,569,243 A | 10/1996 | Kortenbach et al. |
| 5,571,088 A | 11/1996 | Lennox et al. |
| 5,571,215 A | 11/1996 | Sterman et al. |
| 5,573,424 A | 11/1996 | Poppe |
| 5,573,532 A | 11/1996 | Chang et al. |
| 5,575,766 A | 11/1996 | Swartz et al. |
| 5,575,788 A | 11/1996 | Baker et al. |
| 5,575,810 A | 11/1996 | Swanson et al. |
| 5,578,007 A | 11/1996 | Imran |
| 5,582,609 A | 12/1996 | Swanson et al. |
| 5,588,432 A | 12/1996 | Crowley |
| 5,590,657 A | 1/1997 | Cain et al. |
| 5,595,183 A | 1/1997 | Swanson et al. |

(56) References Cited

U.S. PATENT DOCUMENTS

| | | | |
|---|---|---|---|
| 5,599,346 | A | 2/1997 | Edwards et al. |
| 5,605,539 | A | 2/1997 | Buelna et al. |
| 5,607,462 | A | 3/1997 | Imran |
| 5,617,854 | A | 4/1997 | Munsif |
| 5,630,837 | A | 5/1997 | Crowley |
| 5,637,090 | A | 6/1997 | McGee et al. |
| 5,643,197 | A | 7/1997 | Brucker et al. |
| 5,647,869 | A | 7/1997 | Goble et al. |
| 5,656,029 | A | 8/1997 | Imran et al. |
| 5,658,278 | A | 8/1997 | Imran et al. |
| 5,671,747 | A | 9/1997 | Connor |
| 5,673,695 | A | 10/1997 | McGee et al. |
| 5,676,662 | A | 10/1997 | Fleischhacker et al. |
| 5,676,692 | A | 10/1997 | Sanghvi et al. |
| 5,676,693 | A | 10/1997 | Lafontaine |
| 5,678,550 | A | 10/1997 | Bassen et al. |
| 5,680,860 | A | 10/1997 | Imran |
| 5,681,278 | A | 10/1997 | Igo et al. |
| 5,681,294 | A | 10/1997 | Osborne et al. |
| 5,681,308 | A | 10/1997 | Edwards et al. |
| 5,687,723 | A * | 11/1997 | Avitall .................... 600/374 |
| 5,687,737 | A | 11/1997 | Branham et al. |
| 5,688,267 | A | 11/1997 | Panescu et al. |
| 5,690,611 | A | 11/1997 | Swartz et al. |
| 5,697,536 | A | 12/1997 | Eggers et al. |
| 5,697,882 | A | 12/1997 | Eggers et al. |
| 5,697,925 | A | 12/1997 | Taylor |
| 5,697,927 | A | 12/1997 | Imran et al. |
| 5,697,928 | A | 12/1997 | Walcott et al. |
| 5,713,942 | A | 2/1998 | Stern |
| 5,716,389 | A | 2/1998 | Walinsky et al. |
| 5,718,241 | A | 2/1998 | Ben-Haim et al. |
| 5,718,701 | A | 2/1998 | Shai et al. |
| 5,720,775 | A | 2/1998 | Larnard |
| 5,722,402 | A | 3/1998 | Swanson et al. |
| 5,730,074 | A | 3/1998 | Peter |
| 5,730,127 | A | 3/1998 | Avitall |
| 5,730,704 | A | 3/1998 | Avitall |
| 5,733,280 | A | 3/1998 | Avitall |
| 5,735,280 | A | 4/1998 | Sherman et al. |
| 5,743,903 | A | 4/1998 | Stern et al. |
| 5,755,760 | A | 5/1998 | Maguire et al. |
| 5,766,167 | A | 6/1998 | Eggers et al. |
| 5,769,846 | A | 6/1998 | Edwards et al. |
| 5,782,828 | A | 7/1998 | Chen et al. |
| 5,785,706 | A | 7/1998 | Bednarek |
| 5,788,636 | A | 8/1998 | Curley |
| 5,792,140 | A | 8/1998 | Tu et al. |
| 5,797,905 | A | 8/1998 | Fleischman et al. |
| 5,797,960 | A | 8/1998 | Stevens et al. |
| 5,800,428 | A | 9/1998 | Nelson et al. |
| 5,800,482 | A | 9/1998 | Pomeranz et al. |
| 5,810,764 | A | 9/1998 | Eggers et al. |
| 5,810,802 | A | 9/1998 | Panescu et al. |
| 5,827,216 | A | 10/1998 | Igo et al. |
| 5,836,947 | A | 11/1998 | Fleischman et al. |
| 5,840,030 | A | 11/1998 | Ferek-Petric et al. |
| 5,843,021 | A | 12/1998 | Edwards et al. |
| 5,843,152 | A | 12/1998 | Tu et al. |
| 5,844,349 | A | 12/1998 | Oakley et al. |
| 5,846,187 | A | 12/1998 | Wells et al. |
| 5,846,191 | A | 12/1998 | Wells et al. |
| 5,849,028 | A | 12/1998 | Chen |
| 5,860,951 | A * | 1/1999 | Eggers et al. .................. 604/510 |
| 5,861,021 | A | 1/1999 | Thome et al. |
| 5,871,523 | A | 2/1999 | Fleischman et al. |
| 5,871,525 | A | 2/1999 | Edwards et al. |
| 5,871,530 | A * | 2/1999 | Williams et al. .............. 607/122 |
| 5,873,845 | A | 2/1999 | Cline et al. |
| 5,876,399 | A | 3/1999 | Chia et al. |
| 5,879,295 | A | 3/1999 | Li et al. |
| 5,879,296 | A | 3/1999 | Ockuly et al. |
| 5,879,348 | A | 3/1999 | Owens et al. |
| 5,881,732 | A | 3/1999 | Sung et al. |
| 5,882,346 | A | 3/1999 | Pomeranz et al. |
| 5,885,278 | A | 3/1999 | Fleischman |
| 5,891,142 | A | 4/1999 | Eggers et al. |
| 5,893,848 | A | 4/1999 | Negus et al. |
| 5,895,355 | A | 4/1999 | Schaer |
| 5,895,417 | A | 4/1999 | Pomeranz et al. |
| 5,897,553 | A | 4/1999 | Mulier |
| 5,897,554 | A | 4/1999 | Chia et al. |
| 5,899,898 | A | 5/1999 | Arless et al. |
| 5,899,899 | A | 5/1999 | Arless et al. |
| 5,902,289 | A | 5/1999 | Swartz et al. |
| 5,904,711 | A | 5/1999 | Flom et al. |
| 5,906,580 | A | 5/1999 | Kline-Schoder et al. |
| 5,906,587 | A | 5/1999 | Zimmon |
| 5,906,606 | A | 5/1999 | Chee et al. |
| 5,908,029 | A | 6/1999 | Knudson et al. |
| 5,913,854 | A | 6/1999 | Maguire et al. |
| 5,916,213 | A | 6/1999 | Haissaguerre et al. |
| 5,916,214 | A | 6/1999 | Cosio et al. |
| 5,921,924 | A | 7/1999 | Avitall |
| 5,921,982 | A | 7/1999 | Lesh et al. |
| 5,925,045 | A | 7/1999 | Reimels et al. |
| 5,927,284 | A | 7/1999 | Borst et al. |
| 5,928,191 | A | 7/1999 | Houser et al. |
| 5,931,810 | A | 8/1999 | Grabek |
| 5,931,848 | A | 8/1999 | Saadat |
| 5,935,123 | A | 8/1999 | Edwards et al. |
| 5,944,715 | A | 8/1999 | Goble et al. |
| 5,954,661 | A | 9/1999 | Greenspon et al. |
| 5,957,919 | A | 9/1999 | Laufer |
| 5,971,980 | A | 10/1999 | Sherman |
| 5,971,983 | A | 10/1999 | Lesh |
| 5,980,516 | A | 11/1999 | Mulier et al. |
| 5,989,248 | A | 11/1999 | Tu et al. |
| 5,993,412 | A | 11/1999 | Deily et al. |
| 5,993,447 | A | 11/1999 | Blewett et al. |
| 6,004,316 | A | 12/1999 | Laufer |
| 6,004,319 | A | 12/1999 | Goble et al. |
| 6,007,499 | A | 12/1999 | Martin et al. |
| 6,010,500 | A | 1/2000 | Sherman et al. |
| 6,012,457 | A | 1/2000 | Lesh |
| 6,015,391 | A | 1/2000 | Rishton et al. |
| 6,016,811 | A | 1/2000 | Knopp et al. |
| 6,018,676 | A | 1/2000 | Davis et al. |
| 6,019,757 | A | 2/2000 | Scheldrup |
| 6,024,733 | A | 2/2000 | Eggers et al. |
| 6,030,381 | A | 2/2000 | Jones et al. |
| 6,036,687 | A | 3/2000 | Laufer et al. |
| 6,042,556 | A | 3/2000 | Beach et al. |
| 6,048,333 | A | 4/2000 | Lennox et al. |
| 6,056,744 | A | 5/2000 | Edwards |
| 6,056,745 | A | 5/2000 | Panescu et al. |
| 6,056,746 | A | 5/2000 | Goble |
| 6,056,747 | A | 5/2000 | Saadat et al. |
| 6,063,081 | A | 5/2000 | Mulier |
| 6,066,139 | A | 5/2000 | Ryan et al. |
| 6,068,653 | A | 5/2000 | LaFontaine |
| 6,071,279 | A | 6/2000 | Whayne et al. |
| 6,083,237 | A | 7/2000 | Huitema et al. |
| 6,086,585 | A | 7/2000 | Hovda et al. |
| 6,088,894 | A | 7/2000 | Oakley |
| 6,096,037 | A | 8/2000 | Mulier |
| 6,113,592 | A | 9/2000 | Taylor |
| 6,113,596 | A | 9/2000 | Hooven et al. |
| 6,115,523 | A * | 9/2000 | Choi et al. .................... 385/116 |
| 6,117,101 | A | 9/2000 | Diederich et al. |
| 6,120,496 | A | 9/2000 | Whayne et al. |
| 6,141,576 | A | 10/2000 | Littmann et al. |
| 6,142,993 | A | 11/2000 | Whayne et al. |
| 6,142,994 | A | 11/2000 | Swanson et al. |
| 6,149,620 | A | 11/2000 | Baker et al. |
| 6,152,920 | A | 11/2000 | Thompson et al. |
| 6,161,543 | A | 12/2000 | Cox et al. |
| 6,165,174 | A | 12/2000 | Jacobs et al. |
| 6,190,384 | B1 | 2/2001 | Ouchi |
| 6,193,716 | B1 | 2/2001 | Shannon, Jr. |
| 6,210,406 | B1 | 4/2001 | Webster |
| 6,210,410 | B1 | 4/2001 | Farin et al. |
| 6,210,411 | B1 | 4/2001 | Hofmann et al. |
| 6,212,426 | B1 | 4/2001 | Swanson |

(56) References Cited

U.S. PATENT DOCUMENTS

| | | | |
|---|---|---|---|
| 6,217,528 B1 | 4/2001 | Koblish et al. | |
| 6,217,576 B1 | 4/2001 | Tu et al. | |
| 6,224,592 B1 | 5/2001 | Eggers et al. | |
| 6,231,518 B1 | 5/2001 | Grabek et al. | |
| 6,231,591 B1 | 5/2001 | Desai | |
| 6,235,020 B1 | 5/2001 | Cheng et al. | |
| 6,235,024 B1 | 5/2001 | Tu | |
| 6,237,605 B1 | 5/2001 | Vaska et al. | |
| 6,238,347 B1 | 5/2001 | Nix et al. | |
| 6,238,387 B1 | 5/2001 | Miller, III | |
| 6,238,393 B1 | 5/2001 | Mulier | |
| 6,245,061 B1 | 6/2001 | Panescu et al. | |
| 6,245,064 B1 | 6/2001 | Lesh et al. | |
| 6,245,065 B1 | 6/2001 | Panescu et al. | |
| 6,251,092 B1 | 6/2001 | Qin et al. | |
| 6,251,110 B1 | 6/2001 | Wampler | |
| 6,251,128 B1 | 6/2001 | Knopp et al. | |
| 6,258,087 B1 | 7/2001 | Edwards et al. | |
| 6,264,650 B1 | 7/2001 | Hovda et al. | |
| 6,266,551 B1 | 7/2001 | Osadchy et al. | |
| 6,270,471 B1 | 8/2001 | Hechel et al. | |
| 6,283,988 B1 | 9/2001 | Laufer et al. | |
| 6,283,989 B1 | 9/2001 | Laufer et al. | |
| 6,287,304 B1* | 9/2001 | Eggers et al. | 606/37 |
| 6,293,943 B1 | 9/2001 | Panescu et al. | |
| 6,296,619 B1 | 10/2001 | Brisken et al. | |
| 6,299,633 B1 | 10/2001 | Laufer | |
| 6,302,880 B1 | 10/2001 | Schaer | |
| 6,311,692 B1 | 11/2001 | Vaska et al. | |
| 6,312,383 B1 | 11/2001 | Lizzi et al. | |
| 6,314,962 B1 | 11/2001 | Vaska et al. | |
| 6,314,963 B1 | 11/2001 | Vaska et al. | |
| 6,322,559 B1 | 11/2001 | Daulton et al. | |
| 6,325,797 B1 | 12/2001 | Stewart et al. | |
| 6,328,735 B1 | 12/2001 | Curley et al. | |
| 6,328,736 B1 | 12/2001 | Mulier | |
| 6,332,881 B1 | 12/2001 | Carner et al. | |
| 6,336,926 B1* | 1/2002 | Goble | 606/34 |
| 6,352,533 B1 | 3/2002 | Ellman et al. | |
| 6,358,248 B1 | 3/2002 | Mulier | |
| 6,361,531 B1* | 3/2002 | Hissong | 606/27 |
| 6,364,876 B1 | 4/2002 | Erb et al. | |
| 6,368,275 B1 | 4/2002 | Sliwa et al. | |
| 6,371,955 B1 | 4/2002 | Fuimaono et al. | |
| 6,371,956 B1 | 4/2002 | Wilson et al. | |
| 6,383,151 B1 | 5/2002 | Diederich et al. | |
| 6,385,472 B1 | 5/2002 | Hall et al. | |
| 6,398,792 B1 | 6/2002 | O'Connor | |
| 6,406,476 B1* | 6/2002 | Kirwan et al. | 606/50 |
| 6,409,722 B1 | 6/2002 | Hoey | |
| 6,413,254 B1 | 7/2002 | Hissong et al. | |
| 6,416,509 B1 | 7/2002 | Goble et al. | |
| 6,419,648 B1 | 7/2002 | Vitek et al. | |
| 6,425,867 B1 | 7/2002 | Vaezy et al. | |
| 6,430,426 B2 | 8/2002 | Avitall | |
| 6,434,430 B2* | 8/2002 | Borgersen et al. | 607/122 |
| 6,440,130 B1 | 8/2002 | Mulier | |
| 6,443,952 B1 | 9/2002 | Mulier | |
| 6,447,507 B1 | 9/2002 | Bednarek et al. | |
| 6,461,314 B1 | 10/2002 | Pant et al. | |
| 6,461,356 B1 | 10/2002 | Patterson | |
| 6,464,700 B1 | 10/2002 | Koblish et al. | |
| 6,471,697 B1 | 10/2002 | Lesh | |
| 6,471,698 B1 | 10/2002 | Edwards et al. | |
| 6,474,340 B1 | 11/2002 | Vaska et al. | |
| 6,475,216 B2 | 11/2002 | Mulier | |
| 6,477,396 B1 | 11/2002 | Mest et al. | |
| 6,478,793 B1 | 11/2002 | Cosman et al. | |
| 6,484,727 B1 | 11/2002 | Vaska et al. | |
| 6,488,678 B2 | 12/2002 | Sherman | |
| 6,488,680 B1 | 12/2002 | Francischelli | |
| 6,497,704 B2 | 12/2002 | Ein-Gal | |
| 6,502,575 B1 | 1/2003 | Jacobs et al. | |
| 6,508,815 B1 | 1/2003 | Strul et al. | |
| 6,514,250 B1 | 2/2003 | Jahns et al. | |
| 6,517,536 B2 | 2/2003 | Hooven et al. | |
| 6,527,767 B2 | 3/2003 | Wang et al. | |
| 6,537,248 B2 | 3/2003 | Mulier et al. | |
| 6,540,742 B1* | 4/2003 | Thomas et al. | 606/41 |
| 6,558,382 B2 | 5/2003 | Jahns | |
| 6,558,385 B1 | 5/2003 | McClurken et al. | |
| 5,697,536 C1 | 6/2003 | Eggers et al. | |
| 6,575,969 B1 | 6/2003 | Rittman, III et al. | |
| 6,579,288 B1* | 6/2003 | Swanson et al. | 606/41 |
| 6,584,360 B2 | 6/2003 | Francischelli | |
| 6,585,732 B2 | 7/2003 | Mulier | |
| 6,602,248 B1 | 8/2003 | Sharps et al. | |
| 6,603,988 B2 | 8/2003 | Dowlatshahi | |
| 6,605,084 B2 | 8/2003 | Acker et al. | |
| 6,610,055 B1 | 8/2003 | Swanson et al. | |
| 6,610,060 B2 | 8/2003 | Mulier | |
| 6,613,048 B2 | 9/2003 | Mulier | |
| 6,629,924 B2* | 10/2003 | Aydelotte | 600/120 |
| 6,635,034 B1 | 10/2003 | Cosmescu | |
| 6,645,199 B1 | 11/2003 | Jenkins et al. | |
| 6,645,202 B1 | 11/2003 | Pless et al. | |
| 6,648,883 B2 | 11/2003 | Francischelli | |
| 6,656,175 B2 | 12/2003 | Francischelli | |
| 6,663,627 B2 | 12/2003 | Francischelli | |
| 6,666,862 B2 | 12/2003 | Jain et al. | |
| 6,679,882 B1 | 1/2004 | Kornerup | |
| 6,682,501 B1 | 1/2004 | Nelson | |
| 6,689,131 B2 | 2/2004 | McClurken | |
| 6,692,450 B1 | 2/2004 | Coleman | |
| 6,699,240 B2 | 3/2004 | Francischelli | |
| 6,702,810 B2 | 3/2004 | McClurken et al. | |
| 6,702,811 B2 | 3/2004 | Stewart et al. | |
| 6,706,038 B2 | 3/2004 | Francischelli | |
| 6,706,039 B2 | 3/2004 | Mulier | |
| 6,716,211 B2 | 4/2004 | Mulier | |
| 6,736,810 B2 | 5/2004 | Hoey | |
| 6,755,827 B2 | 6/2004 | Mulier | |
| 6,764,487 B2 | 7/2004 | Mulier | |
| 6,766,202 B2 | 7/2004 | Underwood et al. | |
| 6,766,817 B2 | 7/2004 | da Silva | |
| 6,773,433 B2 | 8/2004 | Stewart et al. | |
| 6,775,575 B2 | 8/2004 | Bommannan et al. | |
| 6,776,780 B2 | 8/2004 | Mulier | |
| 6,786,906 B1 | 9/2004 | Cobb | |
| 6,807,968 B2 | 10/2004 | Francischelli | |
| 6,827,713 B2 | 12/2004 | Bek et al. | |
| 6,827,715 B2 | 12/2004 | Francischelli | |
| 6,832,996 B2 | 12/2004 | Woloszko et al. | |
| 6,849,073 B2 | 2/2005 | Hoey | |
| 6,849,075 B2* | 2/2005 | Bertolero et al. | 606/41 |
| 6,858,028 B2 | 2/2005 | Mulier | |
| 6,878,141 B1* | 4/2005 | Perkins et al. | 604/516 |
| 6,887,238 B2 | 5/2005 | Jahns | |
| 6,899,711 B2 | 5/2005 | Stewart et al. | |
| 6,911,019 B2 | 6/2005 | Mulier | |
| 6,915,806 B2 | 7/2005 | Pacek et al. | |
| 6,916,318 B2 | 7/2005 | Francischelli | |
| 6,918,404 B2 | 7/2005 | Dias da Silva | |
| 6,936,046 B2 | 8/2005 | Hissong | |
| 6,942,661 B2 | 9/2005 | Swanson | |
| 6,949,097 B2 | 9/2005 | Stewart et al. | |
| 6,949,098 B2 | 9/2005 | Mulier | |
| 6,953,461 B2 | 10/2005 | McClurken et al. | |
| 6,960,205 B2 | 11/2005 | Jahns | |
| 6,962,589 B2 | 11/2005 | Mulier | |
| 6,974,416 B2* | 12/2005 | Booker et al. | 600/459 |
| 7,066,586 B2 | 6/2006 | da Silva | |
| 7,097,644 B2* | 8/2006 | Long | 606/41 |
| 7,115,139 B2 | 10/2006 | McClurken | |
| 7,127,770 B2* | 10/2006 | Clegg et al. | 15/105 |
| 7,156,845 B2 | 1/2007 | Mulier et al. | |
| 7,166,106 B2 | 1/2007 | Bartel et al. | |
| 7,207,471 B2 | 4/2007 | Heinrich et al. | |
| 7,232,440 B2 | 6/2007 | Dumbauld et al. | |
| 7,247,155 B2 | 7/2007 | Hoey et al. | |
| 7,261,711 B2 | 8/2007 | Mulier et al. | |
| 7,309,325 B2 | 12/2007 | Mulier et al. | |
| 7,311,708 B2 | 12/2007 | McClurken | |
| 7,322,974 B2 | 1/2008 | Swoyer et al. | |

(56) References Cited

U.S. PATENT DOCUMENTS

| | | |
|---|---|---|
| 7,361,175 B2 | 4/2008 | Suslov |
| 7,364,579 B2 | 4/2008 | Mulier et al. |
| 7,537,595 B2 | 5/2009 | McClurken |
| 7,542,807 B2 * | 6/2009 | Bertolero et al. ............. 607/119 |
| 7,604,635 B2 | 10/2009 | McClurken et al. |
| 7,645,277 B2 | 1/2010 | McClurken |
| 7,651,494 B2 | 1/2010 | McClurken |
| 7,708,733 B2 * | 5/2010 | Sanders et al. ................. 606/41 |
| 7,736,361 B2 | 6/2010 | Palanker |
| 7,811,282 B2 * | 10/2010 | McClurken .................... 606/49 |
| 7,815,634 B2 | 10/2010 | McClurken et al. |
| 7,909,820 B2 | 3/2011 | Lipson |
| 7,942,872 B2 | 5/2011 | Ein-Gal |
| 7,976,544 B2 | 7/2011 | McClurken |
| 7,998,140 B2 | 8/2011 | McClurken |
| 8,038,670 B2 | 10/2011 | McClurken |
| 8,048,070 B2 | 11/2011 | O'Brien |
| 8,080,009 B2 | 12/2011 | Lee et al. |
| 8,083,736 B2 | 12/2011 | Mcclurken et al. |
| 8,105,323 B2 | 1/2012 | Buysse et al. |
| 8,177,783 B2 | 5/2012 | Davison et al. |
| 8,216,233 B2 | 7/2012 | McClurken |
| 8,348,946 B2 | 1/2013 | McClurken |
| 8,361,068 B2 | 1/2013 | McClurken |
| 2002/0002329 A1 * | 1/2002 | Avitall ......................... 600/377 |
| 2002/0049483 A1 | 4/2002 | Knowlton |
| 2002/0062131 A1 | 5/2002 | Gallo, Sr. |
| 2003/0014050 A1 | 1/2003 | Sharkey et al. |
| 2003/0032954 A1 | 2/2003 | Carranza et al. |
| 2003/0045872 A1 | 3/2003 | Jacobs |
| 2003/0073993 A1 | 4/2003 | Ciarrocca |
| 2003/0144656 A1 | 7/2003 | Ocel |
| 2003/0191462 A1 | 10/2003 | Jacobs |
| 2003/0204185 A1 | 10/2003 | Sherman et al. |
| 2003/0216724 A1 | 11/2003 | Jahns |
| 2004/0015106 A1 | 1/2004 | Coleman |
| 2004/0015219 A1 | 1/2004 | Francischelli |
| 2004/0024395 A1 | 2/2004 | Ellman et al. |
| 2004/0044340 A1 | 3/2004 | Francischelli |
| 2004/0049179 A1 | 3/2004 | Francischelli |
| 2004/0078069 A1 | 4/2004 | Francischelli |
| 2004/0082948 A1 | 4/2004 | Stewart et al. |
| 2004/0087940 A1 | 5/2004 | Jahns |
| 2004/0092926 A1 | 5/2004 | Hoey |
| 2004/0111136 A1 | 6/2004 | Sharkey et al. |
| 2004/0111137 A1 | 6/2004 | Sharkey et al. |
| 2004/0116923 A1 | 6/2004 | Desinger |
| 2004/0138621 A1 | 7/2004 | Jahns |
| 2004/0138656 A1 | 7/2004 | Francischelli |
| 2004/0143260 A1 | 7/2004 | Francischelli |
| 2004/0186465 A1 | 9/2004 | Francischelli |
| 2004/0215183 A1 | 10/2004 | Hoey |
| 2004/0220560 A1 | 11/2004 | Briscoe |
| 2004/0236322 A1 | 11/2004 | Mulier |
| 2004/0267326 A1 | 12/2004 | Ocel |
| 2005/0010095 A1 | 1/2005 | Stewart et al. |
| 2005/0033280 A1 | 2/2005 | Francischelli |
| 2005/0090815 A1 | 4/2005 | Francischelli |
| 2005/0090816 A1 | 4/2005 | McClurken et al. |
| 2005/0143729 A1 | 6/2005 | Francischelli |
| 2005/0165392 A1 | 7/2005 | Francischelli |
| 2005/0209564 A1 | 9/2005 | Bonner |
| 2005/0267454 A1 | 12/2005 | Hissong |
| 2006/0009756 A1 | 1/2006 | Francischelli |
| 2006/0009759 A1 | 1/2006 | Christian |
| 2006/0041254 A1 | 2/2006 | Francischelli et al. |
| 2006/0064085 A1 | 3/2006 | Schechter et al. |
| 2006/0116675 A1 | 6/2006 | McClurken |
| 2006/0135962 A1 * | 6/2006 | Kick et al. ..................... 606/108 |
| 2006/0149225 A1 | 7/2006 | McClurken |
| 2007/0043397 A1 | 2/2007 | Ocel et al. |
| 2007/0049920 A1 | 3/2007 | McClurken et al. |
| 2007/0093808 A1 | 4/2007 | Mulier et al. |
| 2007/0118114 A1 | 5/2007 | Miller et al. |
| 2007/0149965 A1 | 6/2007 | Gallo, Sr. et al. |
| 2007/0208332 A1 | 9/2007 | Mulier et al. |
| 2008/0004656 A1 | 1/2008 | Livneh |
| 2008/0015563 A1 | 1/2008 | Hoey et al. |
| 2008/0058796 A1 | 3/2008 | O'Brien et al. |
| 2008/0071270 A1 | 3/2008 | Desinger et al. |
| 2008/0103494 A1 | 5/2008 | Rioux et al. |
| 2008/0207028 A1 | 8/2008 | Schutz |
| 2009/0264879 A1 | 10/2009 | Greeley et al. |
| 2009/0306655 A1 | 12/2009 | Stangenes et al. |
| 2010/0069904 A1 | 3/2010 | Cunningham |
| 2010/0100095 A1 | 4/2010 | McClurken et al. |
| 2011/0028965 A1 | 2/2011 | McClurken |
| 2011/0178515 A1 | 7/2011 | Bloom et al. |
| 2011/0196367 A1 | 8/2011 | Gallo |
| 2011/0295249 A1 | 12/2011 | Bloom et al. |
| 2011/0319889 A1 | 12/2011 | Conley et al. |
| 2012/0004657 A1 | 1/2012 | Conley et al. |
| 2012/0101496 A1 | 4/2012 | McClurken et al. |
| 2012/0116397 A1 | 5/2012 | Rencher et al. |
| 2012/0150165 A1 | 6/2012 | Conley et al. |
| 2012/0191084 A1 | 7/2012 | Davison et al. |
| 2012/0253343 A1 | 10/2012 | McClurken et al. |

OTHER PUBLICATIONS

European Office Action dated Nov. 25, 2008 issued in related European Patent Application No. 05851938.0.

* cited by examiner

FLUID-ASSISTED ELECTROSURGICAL DEVICES, METHODS AND SYSTEMS

CROSS REFERENCE TO RELATED APPLICATIONS

This patent application claims priority under 35 U.S.C. §119(e) to U.S. provisional application Ser. No. 61/017,403, filed Dec. 28, 2007, the entire disclosure of which is incorporated by reference herein to the extent it is consistent.

FIELD

This invention relates generally to the field of medical devices, systems and methods for use upon a body during surgery. More particularly, the invention relates to electrosurgical devices, systems and methods for use upon tissues of a human body during surgery, particularly open surgery and minimally invasive surgery such as laparoscopic surgery.

BACKGROUND

A dry tip electrosurgical device, such as a Bovie pencil, can cause the temperature of tissue being treated to rise significantly higher than 100° C., resulting in tissue desiccation, tissue sticking to the electrodes, tissue perforation, char formation and smoke generation.

More recently, fluid-assisted electrosurgical devices have been developed which use saline to inhibit undesirable effects such as tissue desiccation, electrode sticking, smoke production and char formation. However, what is needed is a fluid-assisted electrosurgical device which provides surgeons greater flexibility in accessing treatment locations during surgical procedures.

SUMMARY OF THE INVENTION

This invention, in one embodiment, provides a fluid-assisted bipolar electrosurgical device to treat tissue in a presence of radio frequency energy and a fluid provided from the device. The device comprises a first electrode and a second electrode at the end of a malleable shaft assembly to be hand shapeable by a user of the device, and at least one fluid outlet. The malleable shaft assembly comprises a first shaft and a second shaft, a length of the first shaft and a length of the second shaft in an outer member comprising a polymer, and at least a portion of the first shaft and at least a portion of the second shaft being malleable.

In another embodiment, the invention provides a bipolar electrosurgical device to treat tissue by moving along a tissue surface in a presence of radio frequency energy and a fluid provided simultaneously from the device. The device comprises a first electrode and a second electrode at the end of a malleable shaft assembly to be hand shapeable by a user of the device, and at least one fluid outlet to provide fluid to the first electrode and at least one fluid outlet to provide fluid to the second electrode.

In certain embodiments, the malleable shaft assembly comprises a first shaft and a second shaft, a length of the first shaft and a length of the second shaft in an outer member comprising a polymer, and at least a portion of the first shaft and at least a portion of the second shaft being malleable. In certain embodiments, the polymer may comprise a thermoplastic polymer, an elastomer, a thermoplastic elastomer or an injection molded polymer. In certain embodiments, the outer member provides for a hand shaping of the first shaft and the second shaft simultaneously and with a similar contour.

In certain embodiments, at least one of the first shaft and the second shaft comprises metal, such as stainless steel. In certain embodiments at least a portion of the first shaft is parallel with at least a portion of the second shaft. In other embodiments, at least one of the first electrode and the second electrode is retained at a distal end of the first shaft and the second shaft, respectively.

In certain embodiments, at least one of the first electrode and the second electrode are configured to slide across the tissue surface in the presence of the radio frequency energy and the fluid. In certain embodiments, the first electrode and the second electrode are of substantially a same size and a same shape and laterally spaced from each other. In other embodiments, at least one of the first electrode and the second electrode comprises a surface having a contact angle with the fluid from at least one of the fluid outlets thereon of less than 90 degrees.

In certain embodiments, at least one of the first electrode and the second electrode comprises a domed shape. In other embodiments, at least one of the first electrode and the second electrode comprises a spherical distal end. In certain embodiments, the spherical distal end comprises a hemi-spherical distal end. In other embodiments, the spherical distal end comprises a spherical surface having an arc of about 180 degrees. In certain embodiments, at least one of the first electrode and the second electrode further comprises a cylindrical portion proximal to the spherical distal end.

In certain embodiments, at least one fluid outlet provides fluid to the first electrode proximal and/or adjacent to the spherical distal end of the first electrode and at least one fluid outlet provides fluid to the second electrode proximal and/or adjacent to the spherical distal end of the second electrode. In other embodiments, at least one fluid outlet is at least partially defined by at least one of the first electrode and the second electrode. In still other embodiments, at least one fluid outlet provides fluid to a lateral portion of at least one of the first electrode and the second electrode. In still other embodiments, at least one fluid outlet is located on a lateral portion of the first electrode and the second electrode.

In certain embodiments, the device comprises a first fluid delivery passage in fluid communication with a fluid outlet to provide fluid to the first electrode and a second fluid delivery passage in fluid communication with a fluid outlet to provide fluid to the second electrode. In other embodiments, the first fluid delivery passage passes through a first shaft and the second fluid delivery passage passes through a second shaft. In still other embodiments, the first fluid delivery passage comprises a lumen a first shaft and the second fluid delivery passage comprises a lumen of a second shaft.

In certain embodiments, the device comprises a lighting assembly comprising an illuminator which may be configured to direct illumination towards the first electrode and the second electrode. In certain embodiments, the illuminator is at the end of the malleable shaft assembly. In other embodiments, the illuminator is located in a housing at the end of the malleable shaft assembly, and the housing is at least one of translucent and transparent. When the malleable shaft assembly comprises a first shaft and a second shaft, the illuminator may be between a distal portion of the first shaft and a distal portion of the second shaft or adjacent the distal portion of the first shaft and the distal portion of the second shaft. In other embodiments, the illuminator may be adjacent the first electrode and the second electrode.

In certain embodiments, the illuminator comprises a light source, such as a light emitting diode, or an elongated cylindrical transparent light guide, which may receive light from a light source in a handle of the device and be powered from a power source, such as a battery, also in a handle of the device.

In certain embodiments, the lighting assembly comprises at least one wire conductor in the malleable shaft assembly, and the wire conductor in a sheath in an outer member of the malleable shaft assembly which permits movement of the wire conductor therein.

DETAILED DESCRIPTION

Figure 1:
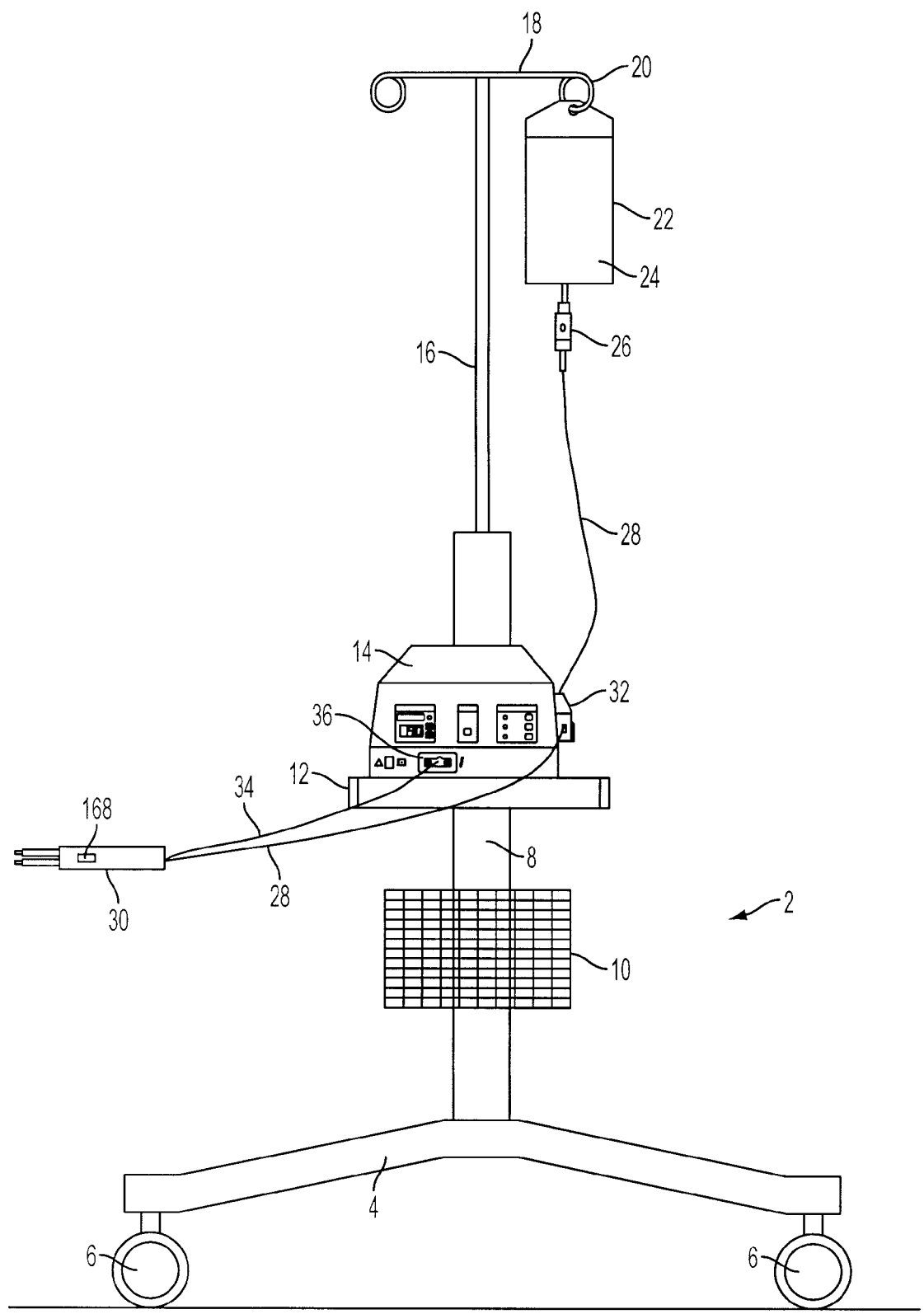
FIG. 1 is a front view of one embodiment of a system of the present invention having an electrosurgical unit in combination with a fluid source and handheld electrosurgical device.

Throughout the description, like reference numerals and letters indicate corresponding structure throughout the several views. Also, any particular feature(s) of a particular exemplary embodiment may be equally applied to any other exemplary embodiment(s) of this specification as suitable. In other words, features between the various exemplary embodiments described herein are interchangeable as suitable, and not exclusive. From the specification, it should be clear that any use of the terms "distal" and "proximal" are made in reference from the user of the device, and not the patient.

The invention provides devices, systems and methods for controlling tissue temperature at a tissue treatment site during an electrosurgical procedure. This is particularly useful for procedures where it is desirable to shrink, coagulate and seal tissue against blood loss, for example, by shrinking lumens of blood vessels (e.g., arteries, veins).

The invention will now be discussed with reference to the figures, with FIG. 1 showing a front view of one embodiment of a system of the present invention having an electrosurgical unit 14 in combination with a fluid source 22 and a handheld electrosurgical device 30. FIG. 1 shows a movable cart 2 having a chassis 4 which is provided with four wheels 6 for easy transportation. The chassis 4 carries a support member 8 comprising a hollow cylindrical post to which a storage basket 10 may be fastened and used to store the electrosurgical unit's user manual, as well as additional unused devices. Furthermore, the support member 8 carries a platform 12 comprising a pedestal table to provide a flat, stable surface for location of the electrosurgical unit 14.

As shown cart 2 further comprises a fluid source carrying pole 16 having a height which may be adjusted by sliding the carrying pole 16 up and down within the support member 8 and thereafter secured in position with a set screw. On the top of the fluid source carrying pole 16 is a cross support 18 provided with loops 20 at the ends thereof to provide a hook for carrying fluid source 22.

As shown in FIG. 1, fluid source 22 comprises a bag of fluid from which the fluid 24 flows through a drip chamber 26 after the bag is penetrated with a spike located at the end of the drip chamber 26. Thereafter, fluid 24 flows through flexible delivery tubing 28 to handheld electrosurgical device 30. Preferably the fluid delivery tubing 28 is made from a polymer material.

Figure 6:
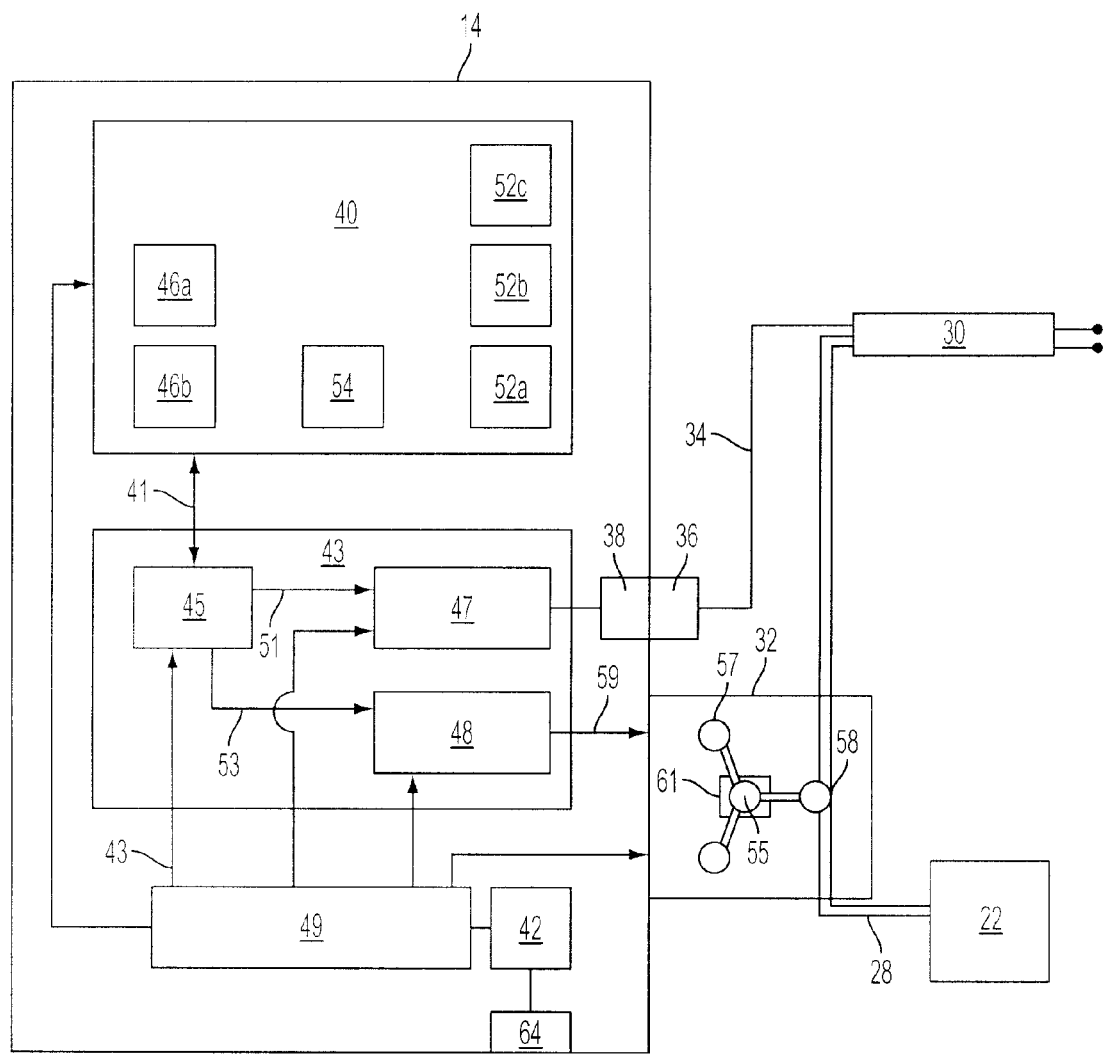
FIG. 6 is a block diagram showing one embodiment of how the electrosurgical unit processes the inputs of RF power setting $P_S$ and the fluid flow rate setting, either $Q_L$, $Q_M$ or $Q_H$, to control the pump speed.

As shown in FIG. 1, the fluid delivery tubing 28 passes through pump 32. As shown pump 32 comprises a peristaltic pump and, more specifically, a rotary peristaltic pump. With a rotary peristaltic pump, a portion of the delivery tubing 28 is loaded into the pump head by raising and lower the pump head in a known manner. As best shown in FIG. 6, fluid 24 is conveyed within the delivery tubing 28 by waves of contraction placed externally on the tubing 28 which are produced mechanically, typically by rotating pinch rollers 57 which rotate on a drive shaft 55 and intermittently compress the tubing 28 against an anvil support 58. Alternatively, pump 32 may comprise a linear peristaltic pump. With a linear peristaltic pump, fluid 24 is conveyed within the delivery tubing 28 by waves of contraction placed externally on the tubing 28 which are produced mechanically, typically by a series of compression fingers or pads which sequentially squeeze the tubing 28 against a support. Peristaltic pumps are generally preferred, as the electromechanical force mechanism, here rollers driven by electric motor, does not make contact the fluid 24, thus reducing the likelihood of inadvertent contamination.

In a preferred embodiment the fluid 24 comprises saline, and even more preferably, normal (physiologic) saline. Although the description herein may make reference to saline as the fluid 24, other electrically conductive fluids can be used in accordance with the invention.

While a conductive fluid is preferred, as will become more apparent with further reading of this specification, fluid 24 may also comprise an electrically non-conductive fluid. The use of a non-conductive fluid is less preferred than a conductive fluid, however, the use of a non-conductive fluid still provides certain advantages over the use of a dry electrode including, for example, reduced occurrence of tissue sticking to the electrode of device 30 and cooling of the electrode and/or tissue. Therefore, it is also within the scope of the invention to include the use of a non-conducting fluid, such as, for example, deionized water.

Figure 2:
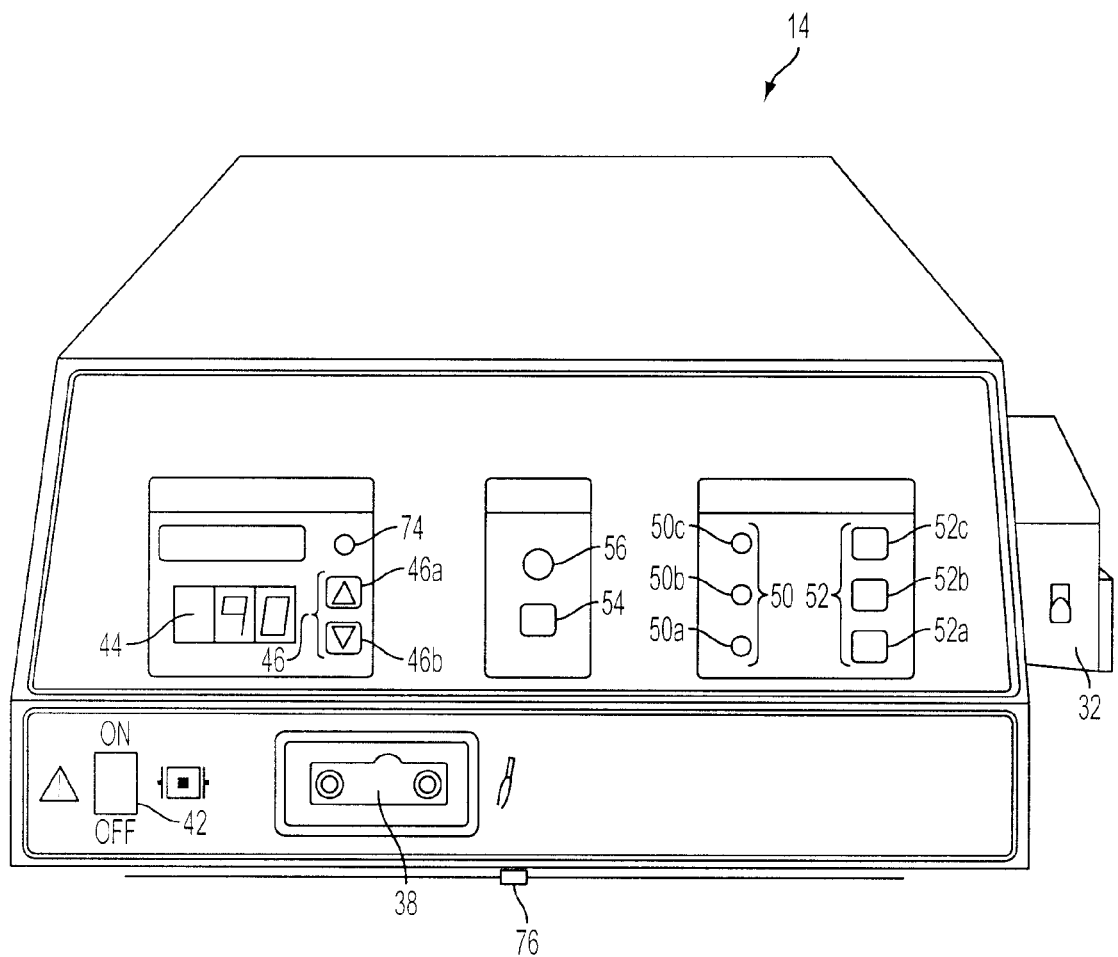
FIG. 2 is a front perspective view of the electrosurgical unit of FIG. 1.

As shown in FIG. 1, electrosurgical device 30 is connected to electrosurgical unit 14 via a cable 34 which comprises a plurality of electrically insulated wire conductors and at least one plug 36 at the end thereof. The electrosurgical unit 14 provides radio-frequency (RF) energy via cable 34 to electrosurgical device 30. As shown in FIG. 2, plug receptacle 38 of electrosurgical unit 14 receives the plug 36 of device 30 therein to electrically connect device 30 to the electrosurgical unit 14. Preferably the fluid delivery tubing 28 is provided as part of cable 34 and produced with the electrically insulated wires via plastic co-extrusion.

FIG. 2 shows the front panel of the electrosurgical unit 14. A power switch 42 is used to turn the electrosurgical unit 14 on and off. After turning the electrosurgical unit 14 on, the RF power setting display 44 is used to display the RF power setting numerically in watts. Preferably the power setting display comprises a liquid crystal display (LCD). Additionally, this display 44 is used to display errors, in which case the display 44 will show "Err" and blink alternately with a special error code number(s).

The RF power selector comprises RF power setting switches 46a, 46b which are used to select the RF power setting. Pushing the switch 46a increases the RF power setting, while pushing the switch 46b decreases the RF power setting. RF power output may be set in 5 watt increments in the range of 20 to 100 watts, and 10 watt increments in the range of 100 to 200 watts. Additionally, electrosurgical unit 14 includes an RF power activation display comprising an indicator light which illuminates when RF power is activated. Switches 46a, 46b may comprise membrane switches.

In addition to having a RF power setting display, electrosurgical unit 14 further includes a fluid flow rate setting display. Flow rate setting display comprises three indicator lights 50a, 50b and 50c with a first light 50a corresponding to a fluid flow rate setting of low, a second light 50b corresponding to a fluid flow rate setting of medium (intermediate) and a third light 50c corresponding to a flow rate setting of high. One of these three indicator lights will illuminate when a fluid flow rate setting is selected.

A fluid flow selector comprising flow rate setting switches 52a, 52b and 52c are used to select or switch the flow rate setting. Three push switches are provided with the first switch 52a corresponding to a fluid flow rate setting of low, the second switch 52b corresponding to a fluid flow rate setting of medium (intermediate) and the third switch 52c corresponding to a flow rate setting of high. Pushing one of these three switches selects the corresponding flow rate setting of either low, medium (intermediate) or high. The medium, or intermediate, flow rate setting is automatically selected as the default setting if no setting is manually selected. Switches 52a, 52b and 52c may comprise membrane switches.

Before starting a surgical procedure, it is desirable to prime device 30 with fluid 24. Priming is desirable to inhibit RF power activation without the presence of fluid 24. A priming switch 54 is used to initiate priming of device 30 with fluid 24. Pushing switch 54 once initiates operation of pump 32 for a predetermined time period to prime device 30. After the time period is complete, the pump 32 shuts off automatically. When priming of device 30 is initiated, a priming display 56 comprising an indicator light illuminates during the priming cycle.

On the front panel the bipolar activation indicator 74 illuminates when RF power is activated from the electrosurgical unit 14, either via a handswitch 168 on device 30 or a footswitch. A pullout drawer 76 is located under the electrosurgical unit 14 where the user of electrosurgical unit 14 may find a short form of the user's manual.

Figure 3:
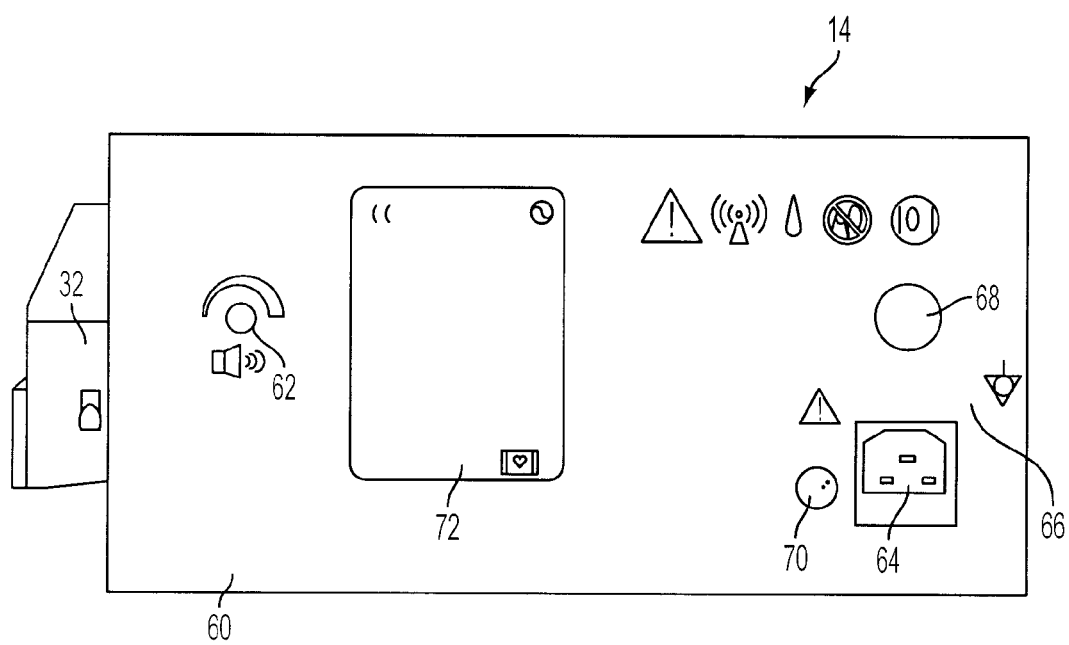
FIG. 3 is a rear view of the electrosurgical unit of FIG. 1.

FIG. 3 shows the rear panel of electrosurgical unit 14. The rear panel of the electrosurgical unit 14 includes a speaker 60 and a volume control knob 62 to adjust the volume of the tone that will sound when the RF power is activated (RF power activation tone). The volume of the RF power activation tone is increased by turning the knob clockwise, and decreased by turning the knob counterclockwise. However, the electrosurgical unit 14 prevents this tone from being completely silenced.

Rear panel of electrosurgical unit 14 also includes a power cord receptacle 64 used to connect the main power cord to the electrosurgical unit 14 and an equipotential grounding lug connector 66 used to connect the electrosurgical unit 14 to earth ground using a suitable cable. The rear panel also includes a removable cap 68 for the installation of a bipolar footswitch socket connectable to an internal footswitch circuit of electrosurgical unit 14 so that the RF power may be activated by a footswitch in addition to a handswitch of device 30. Additionally, the rear panel also includes a fuse drawer 70 which includes which contains two extra fuses, consistent with the line voltage. Finally, the rear panel includes a name plate 72 which may provide information such as the model number, serial number, nominal line voltages, frequency, current and fuse rating information of the electrosurgical unit 14.

Figure 4:
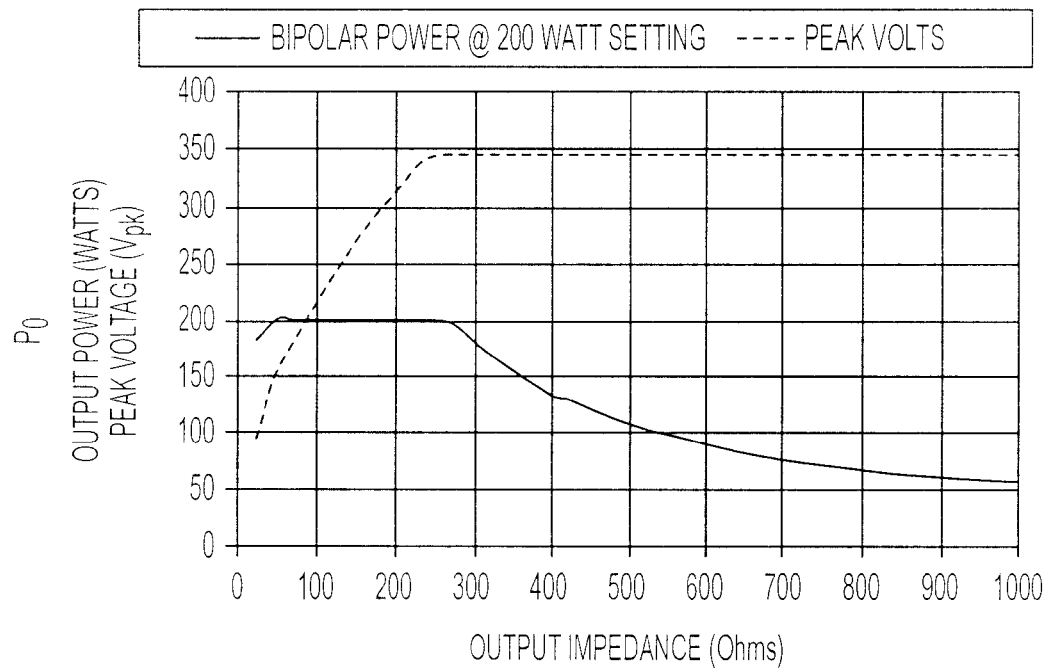
FIG. 4 is a graph of the RF power output versus impedance for the electrosurgical unit of FIG. 1.

The RF power output curve of electrosurgical unit 14 is shown in FIG. 4. Impedance Z, shown in units of ohms on the X-axis and output power $P_O$ is shown in units of watts on the Y-axis. In the illustrated embodiment, the bipolar electrosurgical power (RF) is set to 200 watts. As shown in the figure, for an RF power setting $P_S$ of 200 watts, the output power $P_O$ will remain constant with the set RF power $P_S$ as long as the impedance Z stays between the low impedance cut-off of 30 ohms and the high impedance cut-off of 250 ohms. Below an impedance Z of 30 ohms, the output power $P_O$ will decrease as shown by the low impedance ramp. Above an impedance Z of 250 ohms, the output power $P_O$ will also decrease as shown by the high impedance ramp.

Figure 5:
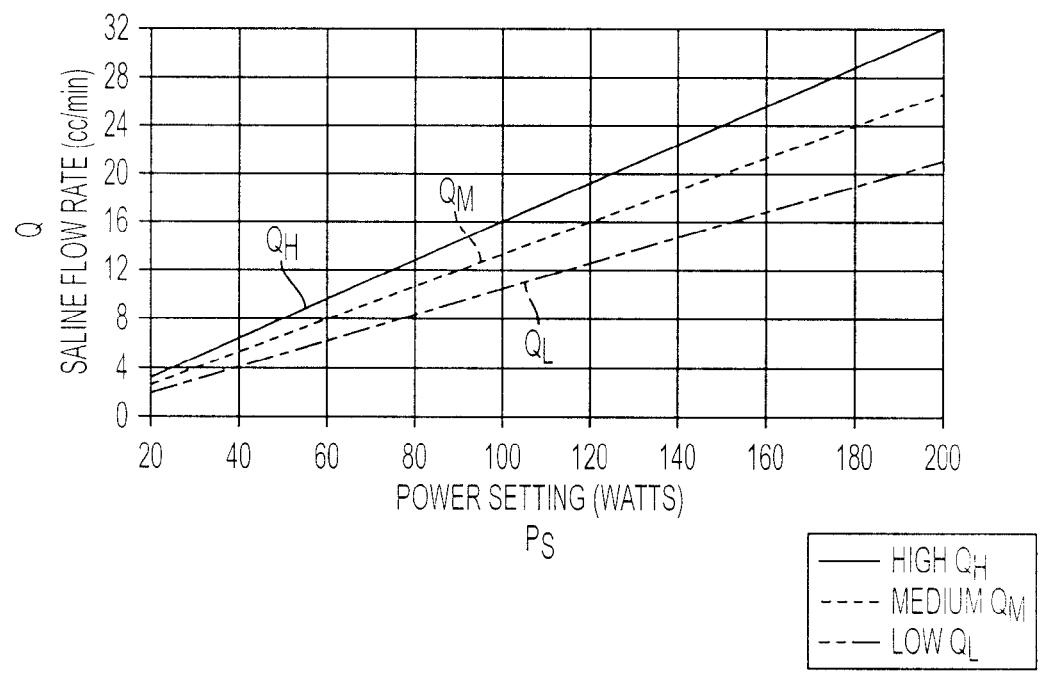
FIG. 5 is graph showing a relationship of fluid flow rate Q in units of cubic centimeters per minute (cc/min) on the Y-axis, and the RF power setting $P_S$ in units of watts on the X-axis.

Electrosurgical unit 14 has also been configured such that the pump speed, and therefore the throughput of fluid expelled by the pump, is predetermined based on two input variables, the RF power setting and the fluid flow rate setting. In FIG. 5 there is shown a relationship of fluid flow rate Q in units of cubic centimeters per minute (cc/min) on the Y-axis, and the RF power setting $P_S$ in units of watts on the X-axis. The relationship has been engineered to inhibit undesirable effects such as tissue desiccation, electrode sticking, smoke production and char formation, while at the same time not providing a fluid flow rate Q at a corresponding RF power setting $P_S$ which is so great as to provide too much electrical dispersion and cooling at the electrode/tissue interface. While not being bound to a particular theory, a more detailed discussion on how the fluid flow rate interacts with the radio frequency power, modes of heat transfer away from the tissue, fractional boiling of the fluid and various control strategies may be found in U.S. Pat. No. 6,702,810, issued Mar. 9, 2004 and U.S. Pat. No. 7,115,139, issued Oct. 3, 2006, both assigned to the assignee of the present invention and hereby incorporated by reference in there entirety to the extent they are consistent.

As shown, electrosurgical unit 14 has been configured to increase the fluid flow rate Q linearly with an increasing RF power setting $P_S$ for each of three fluid flow rate settings of low, medium and high corresponding to $Q_L$, $Q_M$ and $Q_H$, respectively. Conversely, electrosurgical unit 14 has been configured to decrease the fluid flow rate Q linearly with an decrease RF power setting $P_S$ for each of three fluid flow rate settings of low, medium and high corresponding to $Q_L$, $Q_M$ and $Q_H$, respectively. As shown, $Q_L$, $Q_M$ and $Q_H$ can be expressed as a function of the RF power setting $P_S$ by changing exemplary proportionality constants as follows:

$$Q_L = 0.1 \times P_S$$

$$Q_M = 0.1286 \times P_S$$

$$Q_H = 0.1571 \times P_S$$

FIG. 6 shows an exemplary block diagram of how electrosurgical unit 14 processes the inputs of RF power setting $P_S$ and the fluid flow rate setting, either $Q_L$, $Q_M$ or $Q_H$, to control the pump speed, and therefore the throughput of fluid expelled by the pump 32. As shown, user selected input values for the RF power setting $P_S$ and the fluid flow rate setting of either low, medium and high (corresponding to $Q_L$, $Q_M$ and $Q_H$), as well as activating the priming function, are entered into electrosurgical unit 14 by pushing corresponding switches for these parameters positioned on the front panel of the electrosurgical unit 14.

As shown in FIG. 6, the RF power setting switches 46a, 46b, the flow rate setting switches 52a, 52b, 52c and the priming switch 54 are all preferably part of a display panel module 40, preferably comprising a printed circuit board, which receives the inputs into electrosurgical unit 14.

The user selected input values for RF power, fluid flow rate and priming are then conveyed via corresponding input signals 41 to a main module 43 which preferably comprises a printed circuit board including a computer chip 45, a radio-frequency generator 47 and a pump controller 48. As shown, display panel module 40 and main module 43, as well as other components receive power from a power supply module 49, which also comprises a printed circuit board.

Computer chip 45 preferably comprises a micro-processor unit, a memory, and an input/output control unit. In this manner, the functional relationships between the radio-frequency power level and the flow of the fluid may be stored in the memory of the computer chip 45. While the functional relationships are preferably stored in the form of the foregoing equations, they may also be stored as numerical data points as part of a database look-up table.

As shown, the input signals 41 are received and processed by computer chip 45. More specifically, for example, from the input signal received corresponding to the fluid flow rate setting of either $Q_L$, $Q_M$ or $Q_H$, the computer chip 45 may first determine which of the above equations to apply. After determining which equation to apply, computer chip 45 may then apply the relationship to determine the output for flow of the fluid from the pump 32 based on the selected radio-frequency power level. Having determined this output, the computer chip 45 then sends output signals 51 and 53 corresponding to the selected radio-frequency power level and calculated output for flow of the fluid from the pump 32 to the radio-frequency generator 47 and pump controller 48, respectively. Thereafter, the pump controller 48 controls the speed of the pump drive shaft 55 by controlling the input voltage 59 to the pump motor 61 which rotates the drive shaft 55. More detailed drawings of exemplary electrosurgical unit 14 may be found in U.S. Publication No. 2006/0149225, published Jul. 6, 2006, which is assigned to the assignee of the present invention and hereby incorporated by reference in its entirety to the extent it is consistent.

Electrosurgical unit 14 can include a delay mechanism, such as a timer, to automatically keep the fluid flow on for several seconds after the RF power is deactivated to provide a post-treatment cooling. Electrosurgical unit 14 can also include a delay mechanism, such as a timer, to automatically turn on the fluid flow up to several seconds before the RF power is activated to inhibit the possibility of undesirable effects as tissue desiccation, electrode sticking, char formation and smoke production.

Electrosurgical unit 14 is particularly configured for use with bipolar devices. With a bipolar device, an alternating current electrical circuit is created between the first and second electrical poles/electrodes of the device. An exemplary bipolar electrosurgical device of the present invention which may be used in conjunction with electrosurgical unit 14 of the present invention is shown at reference character 30g in FIG. 7. While various electrosurgical devices of the present invention are described herein with reference to use with electrosurgical unit, it should be understood that the description of the combination is for purposes of illustrating the system of the invention. Consequently, it should be understood that while the electrosurgical devices disclosed herein may be preferred for use with electrosurgical unit, it may be plausible to use other electrosurgical devices with electrosurgical unit, or it may be plausible to use the electrosurgical devices disclosed herein with another electrosurgical unit.

Figure 7:
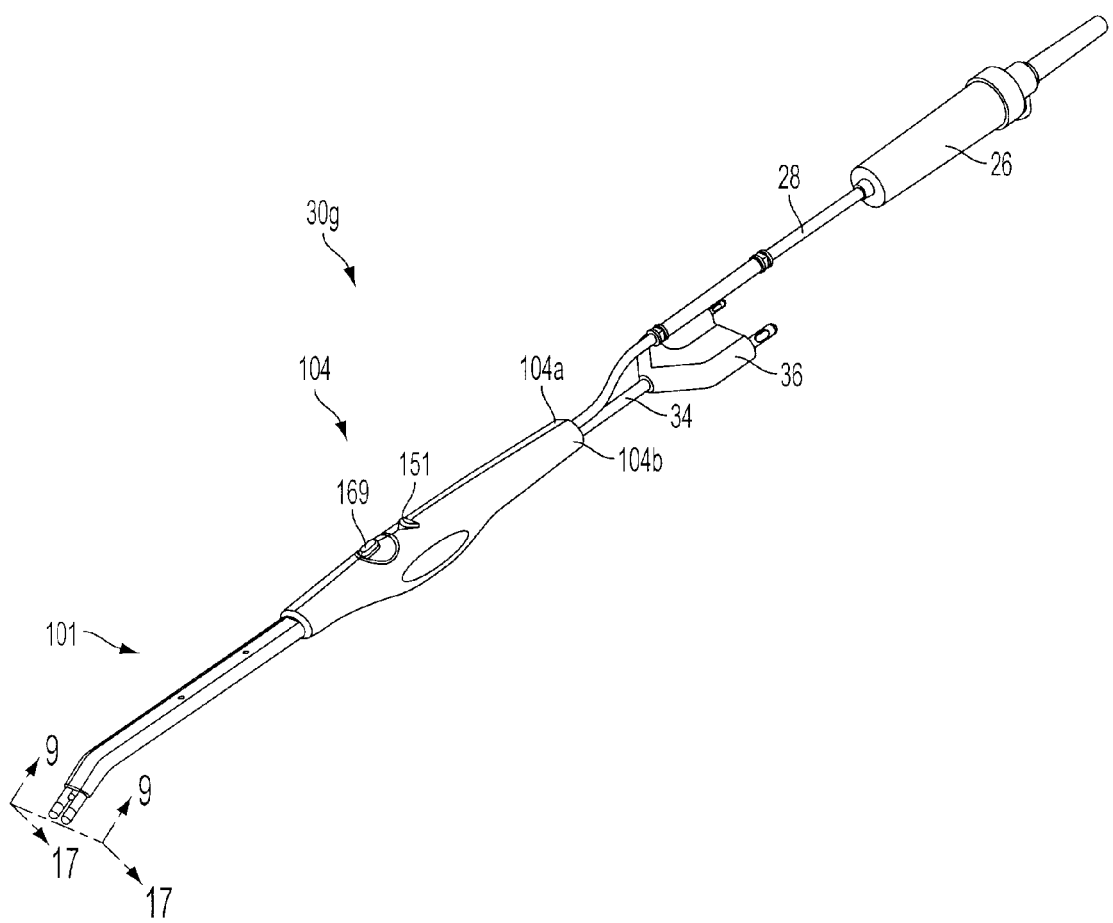
FIG. 7 is a perspective view of an electrosurgical device according to the present invention.

As shown in FIG. 7, exemplary bipolar device 30g comprises a proximal handle 104 comprising mating handle portions 104a, 104b. Handle 104 is preferably made of a sterilizable, rigid, non-conductive material, such as a polymer (e.g., polycarbonate). Also, handle 104 is preferably configured slender, along with the rest of device 30g, to facilitate a user of device 30g to hold and manipulate device 30g like a pen-type device. Device 30g also comprises a cable 34 which is connectable to electrosurgical unit 14 and flexible fluid delivery tubing 28 which is connectable to fluid source 22, preferably via a spike located at the end of drip chamber 26, which respectively provide radio frequency energy and fluid to electrodes 114a, 114b.

Figure 8:
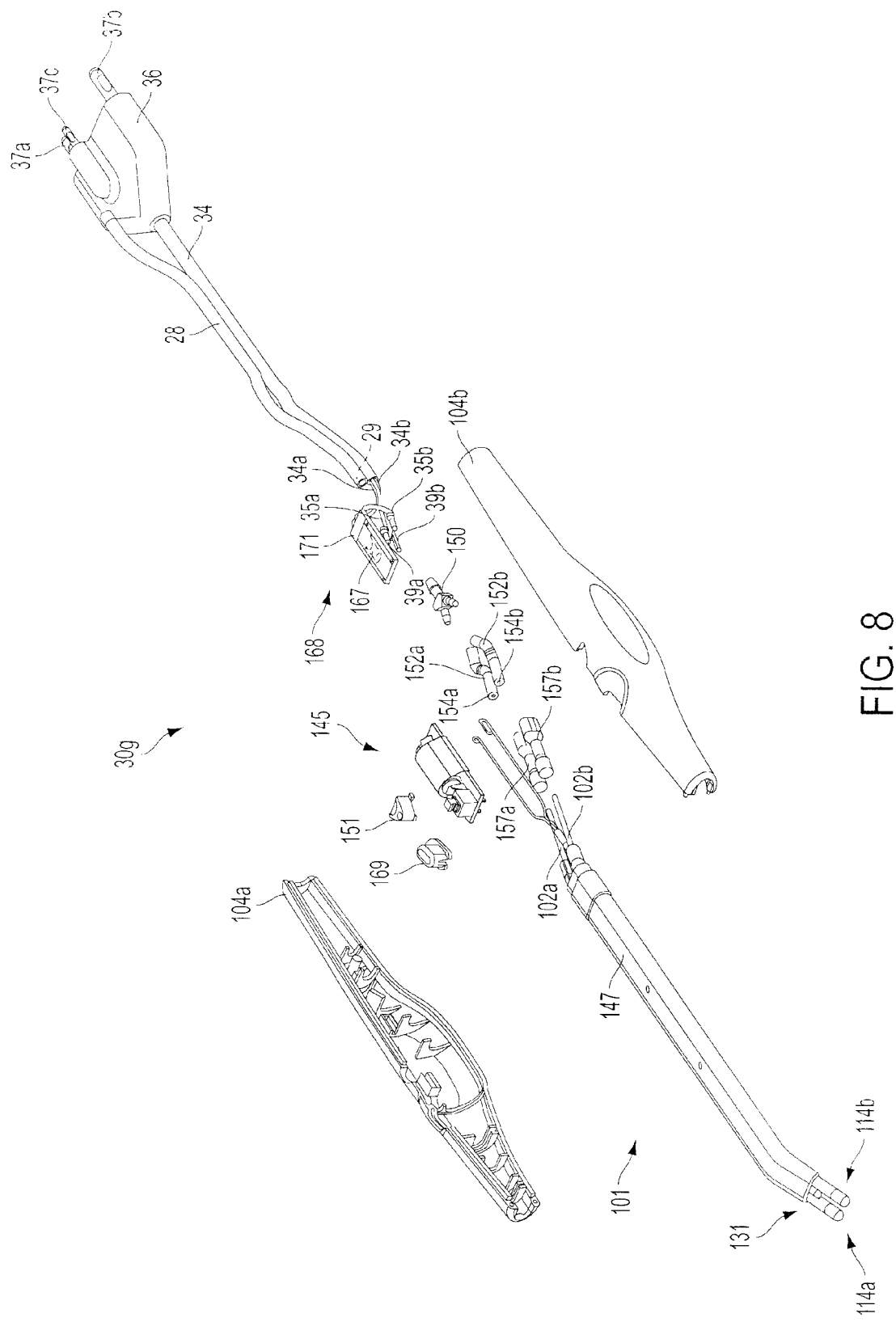
FIG. 8 is an exploded perspective view of the device of FIG. 7.

As best shown in FIG. 8, cable 34 of device 30g comprises three insulated wires 34a, 34b, 34c (hidden by platform 171) connectable to electrosurgical unit 14 via three banana (male) plug connectors 37a, 37b, 37c. The banana plug connectors 37a, 37b, 37c are each assembled with wire conductors 35a, 35b, 35c of insulated wires 34a, 34b, 34c within the housing of plug 36 in a known manner. Wire conductors 35a, 35b, 35c of insulated wires 34a, 34b, 34c are connected distally to a handswitch assembly 168, and thereafter wire conductors 35a, 35b are connected to semi-circular barrel crimp terminals 39a, 39b which snap connect to a proximal portion of shafts 102a, 102b of shaft assembly 101.

Handswitch assembly 168 comprises a push button 169 which overlies a domed switch 167 on a platform 171 comprising a printed circuit board, with the construction and wiring of the handswitch assembly 168 known in the art. Upon depression of button 169, domed switch 167 forms a closed circuit which is sensed by electrosurgical unit 14, which then provides power to the electrodes 114a, 114b. Additional discussion concerning the handswitch may be found in U.S. Publication No. 2006/0149225, published Jul. 6, 2006, and U.S. Publication No. 2005/0090816, published Apr. 28, 2005, which are assigned to the assignee of the present invention and are hereby incorporated by reference in there entirety to the extent they are consistent.

Fluid delivery tubing 28 of device 30g is connected within handle 104 to the inlet branch of a Y-splitter 150, which thereafter provides two outlet branches which are connected to the proximal ends of polymer delivery tubing segments 152a, 152b. The distal ends of delivery tubing segments 152a, 152b are thereafter connected to the proximal ends of shafts 102a, 102b. To connect delivery tubing 152a, 152b to shafts 102a, 102b, the lumens 154a, 154b are preferably interference fit over the outside diameter of shafts 102a, 102b to provide an interference fit seal there between.

Once semi-circular barrel crimp terminals 39a, 39b and delivery tubing segments 152a, 152b are connected to shafts 102a, 102b, a polymer shrink wrap tubing 157a, 157b is then heat shrink wrapped around the connections to better electrically insulate the shafts 102a, 102b and better secure the connections.

Shaft assembly 101 comprises two, preferably parallel, self-supporting, hollow shafts 102a, 102b, which preferably comprise metal such as stainless steel tubing. Retained at and connected to the distal ends of shafts 102a, 102b are two laterally and spatially separated (by empty space) contact elements comprising electrodes 114a, 114b which are configured as mirror images in size and shape, and have a distal end with a surface devoid of edges (to provide a uniform current density) to treat tissue without cutting. Electrodes 114a, 114b preferably comprise an electrically conductive metal. A preferred material is stainless steel. Other suitable materials may include titanium, gold, silver and platinum.

Figure 9:
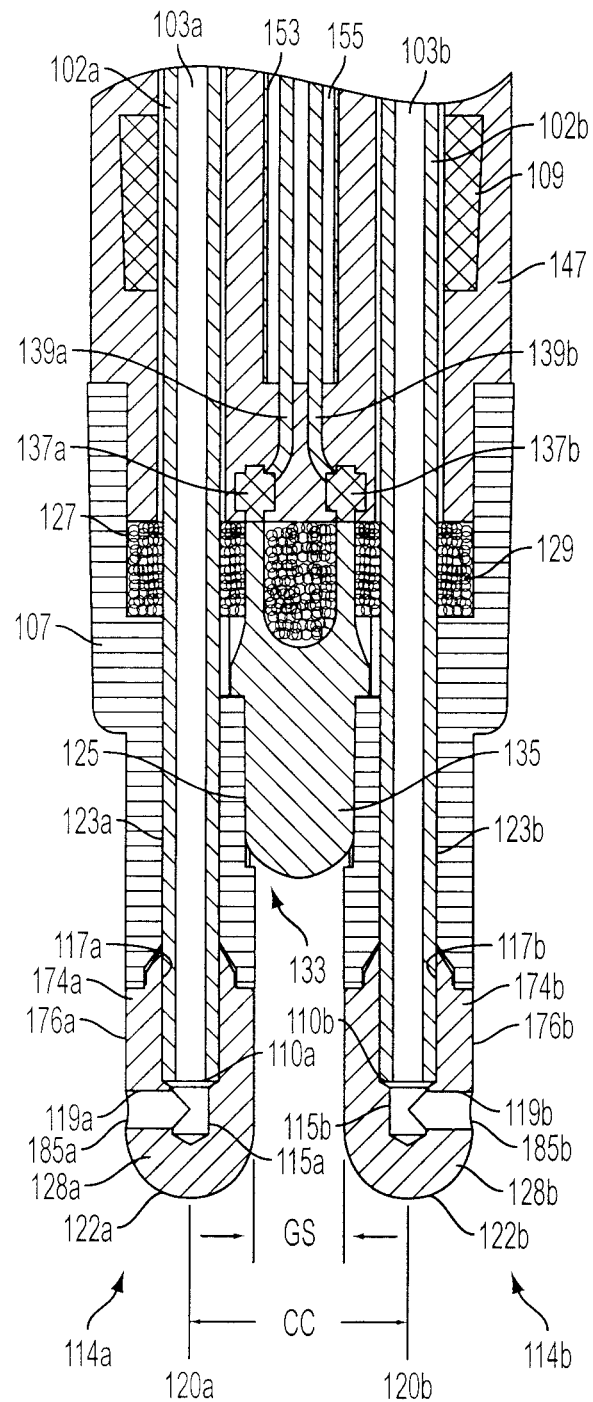
FIG. 9 is a close-up cross-sectional view of the tip portion of the device of FIG. 7 taken along line 9-9 of FIG. 7.

Electrodes 114a, 114b are preferably configured to slide across the tissue surface in the presence of the radio frequency energy from electrosurgical unit 14 and the fluid 24 from the fluid source 22. As best shown in FIG. 9, electrodes 114a, 114b have a domed shaped identified by a spherical portion 128a, 128b and a corresponding spherical surface portion 122a, 122b located at the distal end of device 30g which provide a smooth, blunt contour outer surface which is not pointed or sharp. More specifically, as shown, the spherical portions 128a, 128b and spherical surface portions 122a, 122b provide a hemisphere (i.e., less than a full sphere) and hemispherical surface portion having an arc preferably of about 180 degrees. Preferably the spherical portion 128a, 128b and spherical surface portions 122a, 122b have a uniform radius in the range between and including about 1.25 mm to about 2.5 mm, and more preferably have a radius of about 1.75 mm.

Also as shown, electrodes 114a, 114b each preferably comprise a rectilinear cylindrical portion 174a, 174b and a corresponding cylindrical surface portion 176a, 176b located proximal and adjacent to the spherical portion 128a, 128b and spherical surface portion 122a, 122b, respectively. Preferably cylindrical portions 174a, 174b have a diameter in the range between and including about 2.5 mm to about 5.0 mm, and more preferably have a diameter of about 3.5 mm.

With respect to length, preferably cylindrical portions 174a, 174b have a length in the range between and including about 2 mm to about 6 mm, and more preferably have a length of about 4 mm.

Preferably the longitudinal axes 120a, 120b of electrodes 114a, 114b are separated center-to-center CC about 6.0 mm. As a result, when cylindrical portions 174a 174b have a preferred diameter of 3.5 mm, the actual spatial gap separation GS between electrodes 114a, 114b is about 2.5 mm.

Each electrode 114a, 114b includes a longitudinally oriented linear blind bore 115a, 115b and counter bore 117a, 117b. As shown in FIG. 9, the outside diameter of a distal end portion of each shaft 102a, 102b is configured to extend into counter bore 117a, 117b of electrodes 114a, 114b and fit with the diameter of counter bore 117a, 117b, with the distal end 110a, 110b of each shaft 102a, 102b in contact with the bottom of the counter bore. Preferably the electrodes 114a, 114b and shafts 102a, 102b are then laser welded together. In alternative embodiments, the outside diameter of shafts 102a, 102b may be configured to fit with the diameter of counter bore 117a, 117b to form a press (interference) fit to provide a secure connection. In other alternative embodiments, electrodes 114a, 114b may be assembled to shafts 102a, 102b by threaded engagement. In still other embodiments, electrodes 114a, 114b may be detachably assembled to shafts 102a, 102b such that they may be removed from the shafts 102a, 102b, preferably manually by human hand, so that device 30g may be used with multiple different contact elements/electrodes.

In addition to blind bore 115a, 115b and counterbore 117a, 117b, electrodes 114a, 114b also include a blind bore 119a, 119b, which perpendicularly intersects bore 115a, 115b within cylindrical portion 174a, 174b and provides outlets 185a, 185b for fluid. Thus, during use of device 30g, fluid 24 from fluid source 22 is communicated through a tubular fluid passage provided by lumen 29 of delivery tubing 28, after which it flows through the tubular fluid passages of Y-splitter 150 and then into the lumens 154a, 154b of delivery tubing segments 152a, 152b to the lumens 103a, 103b of shafts 102a, 102b. From lumens 103a, 103b of shafts 102a, 102b, fluid 24 then flows into the tubular passage provided by bore 115a, 115b and then into the tubular passage provided by bore 119a, 119b where it thereafter exits device 30g from fluid outlets 185a, 185b onto electrodes 114a, 114b. As shown in FIG. 9, fluid outlets 185a, 185b are defined by the cylindrical portions 174a, 174b of electrodes 114a, 114b, and fluid outlets 185a, 185b are proximal and adjacent to the spherical portions 128a, 128b of electrodes 114a, 114b. Furthermore, as described in greater detail below, fluid outlets 185a, 185b provide fluid and are located on lateral portions of electrodes 114a, 114b.

The relationship between the material for electrodes 114a, 114b and their surfaces, and fluid 24 throughout the various embodiments should be such that the fluid 24 wets the surface of the electrodes 114a, 114b. Contact angle, θ, is a quantitative measure of the wetting of a solid by a liquid. It is defined geometrically as the angle formed by a liquid at the three phase boundary where a liquid, gas and solid intersect. In terms of the thermodynamics of the materials involved, contact angle θ involves the interfacial free energies between the three phases given by the equation $$\gamma_{LV}\cos\theta = \gamma_{SV} - \gamma_{SL}$$

where $\gamma_{LV}$, $\gamma_{SV}$ and $\gamma_{SL}$ refer to the interfacial energies of the liquid/vapor, solid/vapor and solid/liquid interfaces, respectively. If the contact angle θ is less than 90 degrees the liquid is said to wet the solid. If the contact angle is greater than 90 degrees the liquid is non-wetting. A zero contact angle θ represents complete wetting. Thus, preferably the contact angle is less than 90 degrees.

After assembly of electrodes 114a, 114b with shafts 102a, 102b, the two electrode/shaft subassemblies are then preferably assembled to nosepiece 107, with the proximal ends of each shaft 102a, 102b inserted into the distal end of shaft aperture 123a, 123b of nosepiece 107. Each electrode/shaft subassembly is extended through shaft aperture 123a, 123b until the proximal end of each electrode 114a, 114b makes interference contact with the distal end of nosepiece 107. Among other things, nosepiece 107 provides a housing, particularly for a light assembly discussed below, and holds the electrodes 114a, 114b stationary at the designed separation distance and proper orientation. Nosepiece 107 preferably comprises a rigid polymer material, and more preferably comprises acrylonitrile-butadiene-styrene (ABS).

Figure 10:
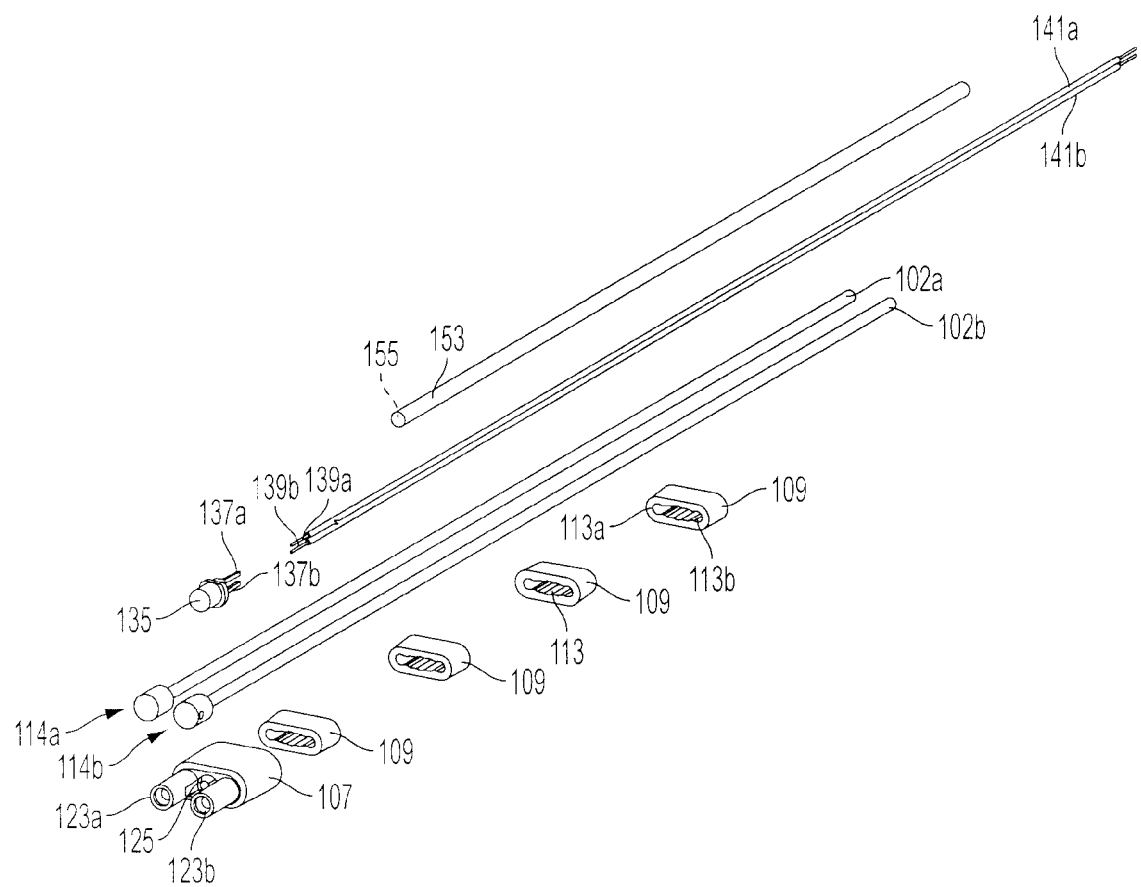
FIG. 10 is an exploded perspective view of various components of the shaft assembly of the device of FIG. 7.
Figure 11:
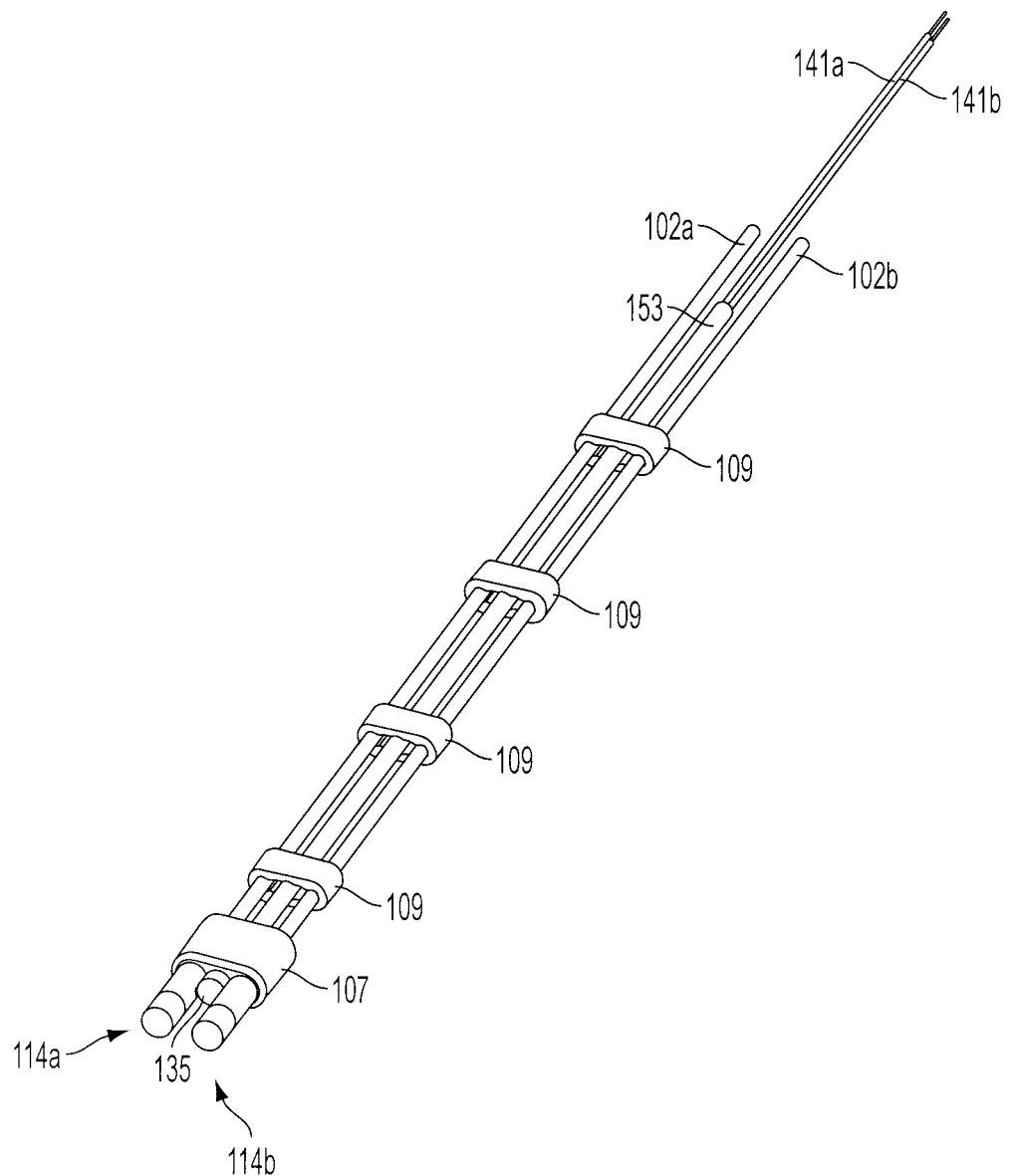
FIG. 11 is an assembled perspective view of various components of the shaft assembly of the device of FIG. 7.

As shown in FIGS. 10 and 11, proximal to nosepiece 107, shafts 102a, 102b are retained in position relative to each other upon being assembled in C-shaped portion 113a, 113b of an aperture 113 of one or more retaining clips 109. Retaining clips 109 are assembled to shafts 102a, 102b after the electrode/shaft subassemblies are inserted and seated relative to nosepiece 107. As best shown in FIG. 11, once the clips 109 are connected to the shafts 102a, 102b, preferably by a snap-fit connection, the clips 109 may be configured to slide along the length of the shafts 102a, 102b as to adjust or vary the location of the clips 109 on the shafts 102a, 102b. Once the clips 109 are properly positioned, they may then be held in fixed position relative to shafts 102a, 102b by the use of an adhesive. The retaining clips 109 preferably comprise a polymer material, and more preferably comprise acrylonitrile-butadiene-styrene (ABS).

At the end of shaft assembly 101, device 30g also preferably includes a lighting assembly comprising an illuminator 131 (shown in FIG. 7), which comprises a light source configured to direct illumination towards the electrodes 114a, 114b. As shown in FIG. 9, illuminator 131 preferably comprises a light emitting diode (LED) 133. LED 133 includes a lens 135 having a spherical distal end and terminals 137a, 137b. In this embodiment, LED 133 is preferably located between and adjacent a distal portion of shafts 102a, 102b and slightly proximally adjacent to the electrodes 114a, 114b (about 0.125 inches to 2 inches, and more preferably about 0.25 inches to 1 inch, and even more preferably about 0.375 inches) to provide bright illumination primarily between the electrodes 114a, 114b, while at the same time minimizing the shadows caused by the electrodes 114a, 114b and the likelihood of blood contamination during use. Furthermore, nosepiece 107 may also be made translucent or transparent to further reduce shadows. Also, lens 135 preferably emits white light and has a half intensity angle of about 15 to 20 degrees.

Figure 13:
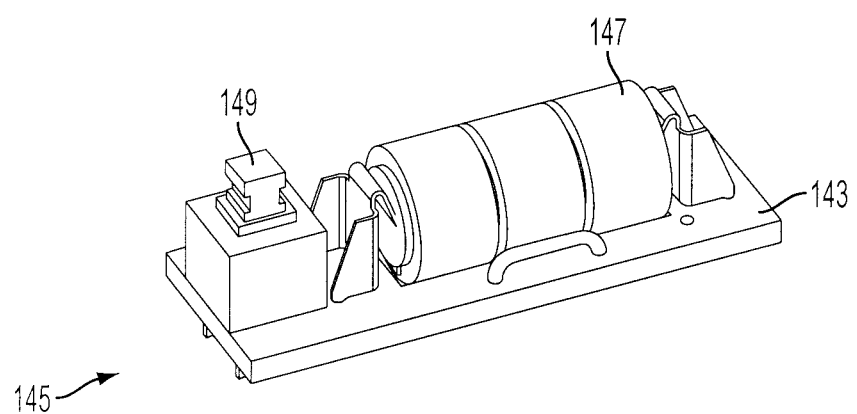
FIG. 13 is a close-up perspective view of the activation assembly for the light assembly.

Also as shown in FIG. 9, terminals 137a, 137b are connected, preferably by resistance welding, to the distal ends of wire conductors 139a, 139b of insulated wires 141a, 141b. In order to provide electrical power to LED 133, the proximal ends of wire conductors 139a, 139b are connected, preferably by soldering, to a printed circuit board 143 of an activation assembly 145. As best shown in FIG. 13, activation assembly 145 includes a power source 147 preferably comprising a plurality of batteries provided in series relationship which provide power to LED 133 in response to the formation of a closed circuit with wire conductors 139a, 139b when switch 149 is in a depressed position in response to the pressing of button 151 (shown in FIG. 8). In this manner, the light source operates independent of the power of the electrosurgical unit 14 and may also be activated simultaneously with the RF power from electrosurgical unit 14.

Returning to FIGS. 10 and 11, during assembly of device 30g, after LED terminals 137a, 137b are connected to wire conductors 139a, 139b of insulated wires 141a, 141b, insulated wires 141a, 141b are then passed through the lumen 155 of a hollow polymer tubing 153 which provides a sheath. LED 133, insulated wires 141a, 141b and the polymer tubing 153 are then loaded into a portion of aperture 113 of retaining clips 111 between shafts 102a, 102b. In this manner, as shown in FIG. 11, the insulated wires 141a, 141b within the polymer tubing 153 are retained in position between shafts 102a, 102b. Thereafter LED 133 is inserted into the LED aperture 125 of nosepiece 107 which is located between the apertures 123a, 123b for shafts 102a, 102b.

As best shown in FIG. 9, in order to further retain shafts 102a, 102b and LED 133 relative to nosepiece 107, cavity 127 of nosepiece is partially filled with a potting material 129. Potting material 129 preferably comprises a polymer material, and more preferably comprises an ultraviolet cured thermoset epoxy.

Figure 12:
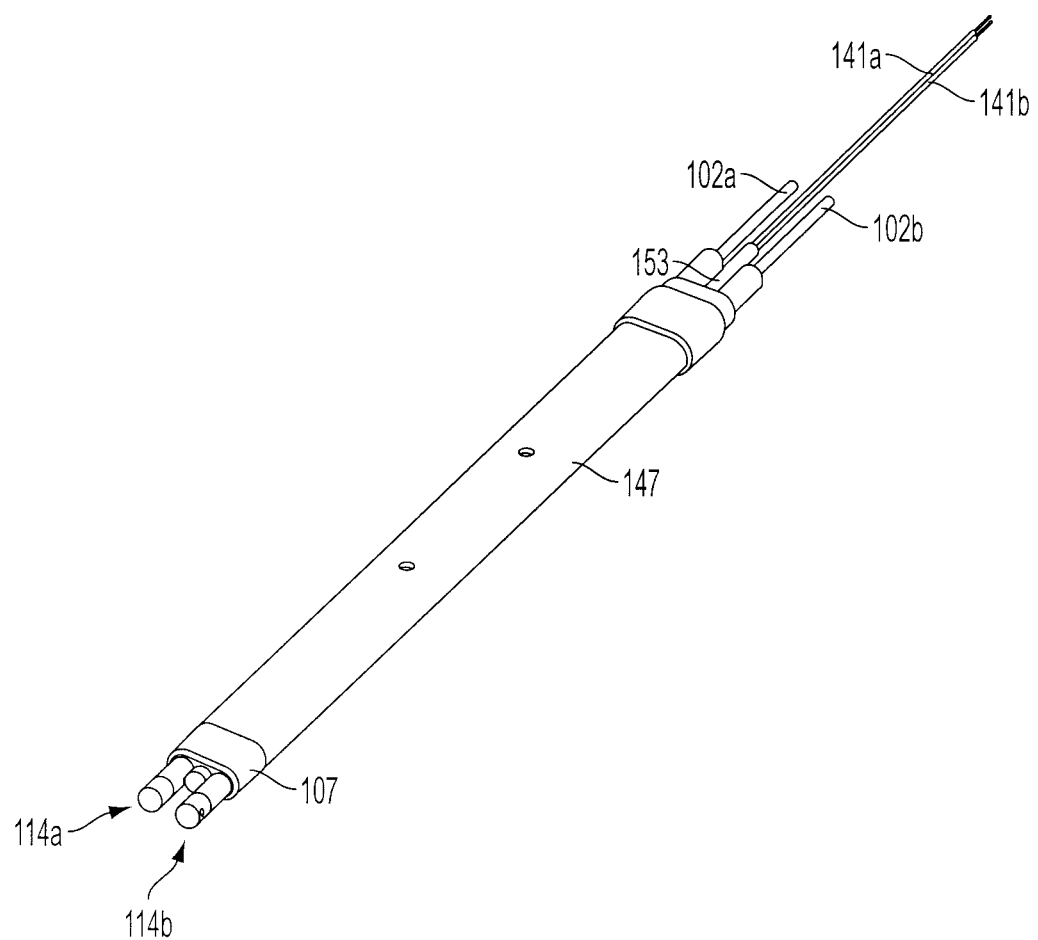
FIG. 12 is an assembled perspective view of the shaft assembly of the device of FIG. 7.

As shown in FIGS. 9 and 12, proximal to potting material 129, a portion of the lengths of shafts 102a, 102b and polymer tubing 153 are surrounded by and encapsulated in an common outer member 147, which preferably comprises a flexible polymer. Outer member 147 electrically insulates the exposed length of shafts 102a, 102b between potting material 129 and handle 104. Furthermore, similar to clips 111, outer member 147 retains shafts 102a, 102b and polymer tube 153 in position relative to each other.

Outer member 147 is preferably formed by injection molding. During the injection molding process, the sub-assembly shown in FIG. 11, comprising electrodes 114a, 114b; shafts 102a, 102b; nosepiece 107; retaining clips 109; LED 133; insulated wires 141a, 141b; polymer tubing 153; and potting material 129 is placed in the injection mold prior to the introduction of polymer. Thereafter, the mold is closed and preferably thermoplastic polymer, and more preferably a thermoplastic elastomer, is injected into the unoccupied portions of the mold cavity to overmold and mold-in place portions of the sub-assembly as shown in FIG. 12. Even more preferably, the thermoplastic elastomer has a Shore A durometer of 90-95 and comprises a thermoplastic rubber.

As indicated above, prior to the injection molding process, retainer clips 111 provide the benefit of retaining shafts 102a, 102b and polymer tube 153 in position relative to each other. Furthermore, during the injection molding process, retainer clips 111 provide the added benefit of locating the shafts 102a, 102b and polymer tube 153 in the middle of the mold cavity away from the surface of the mold to better ensure that the shafts 102a, 102b and polymer tube 153 are centrally located within the polymer molding.

Also, potting material 129, in addition to retaining shafts 102a, 102b and LED 133 relative to nosepiece 107 prior to injection molding, provides the added benefit of inhibiting the injected thermoplastic from entering shaft apertures 123a, 123b and LED aperture 125 of nosepiece 107. However, in certain embodiments not utilizing a light source, the potting material 129, as well as the nosepiece 107, may be eliminated.

To be hand shapeable by surgeons and other users of device 30g, so that the device 30g may be used in a greater multitude of angles and locations, at least a portion of shafts 102a, 102b of device 30g are preferably malleable to provide a malleable shaft assembly 101. Also, in this manner, a distal portion of shafts 102a, 102b, as shown in FIG. 8, may be bendable at an angle relative to the longitudinal axis of the proximal portion of shafts 102a, 102b during manufacturing of device 30g so they may be provided to users of device 30g at various angles. For example, angle may range from about 5 degrees to 90 degrees, and more preferably, about 15 degrees to 45 degrees, and even more preferably about 30 degrees. As used herein, malleable means able to be shaped, particularly by bending (without a mechanical mechanism, such as a hinge or joint).

Outer member 147, in addition to electrically insulating shafts 102a, 102b from one another, has been found to be particularly useful in facilitating the hand shaping of shafts 102a, 102b of shaft assembly 101 simultaneously and with a similar contour without cracking. In this manner surgeons and other users of device 30g need not bend the shafts 102a, 102b individually. Also, hollow tube 153, by providing a sheath for wires 141a, 141b in outer member 147 which permits movement of the wires 141a, 141b, also facilitates the hand shaping of shaft assembly 101. Hollow tube 153 prevents outer member 147 from molding directly to insulated wires 141a, 141b, which could caused conductors 139a, 139b to break during the shaping of shaft assembly 101 if not permitted to move independently and freely within the lumen 155 of tubing 153.

To provide malleability, shafts 102a, 102b preferably have an outer wall diameter of about 0.063 inches and an inner wall diameter of about 0.032 inches. Shafts 102a, 102b also preferably are made from 304 stainless steel with a temper from about ½ to ¾ hard (130,000 to 150,000 psi. (pounds per square inch) tensile strength) and an elongation at break of about 40%. Shafts 102a, 102b with the foregoing properties provide sufficient stiffness as not to be too pliable during normal use of device 30g, while at the same time inhibiting the shafts 102a, 102b from kinking or breaking when shaped for application. When the wall thickness is too thin, shafts 102a, 102b may kink, and when the wall thickness is too thick, the shafts 102a, 102b may be too stiff. Furthermore, a shaft 102a, 102b with a larger diameter may also kink more than a shaft of smaller diameter. Shafts 102a, 102b may also be malleable for a portion of the length or full length depending on application. For example, the shafts 102a, 102b can be made with variable stiffness along the length and be malleable only for a distal portion thereof. Preferably this is performed by controlled annealing of the shafts 102a, 102b only in the area where malleability is desired.

Figure 15:
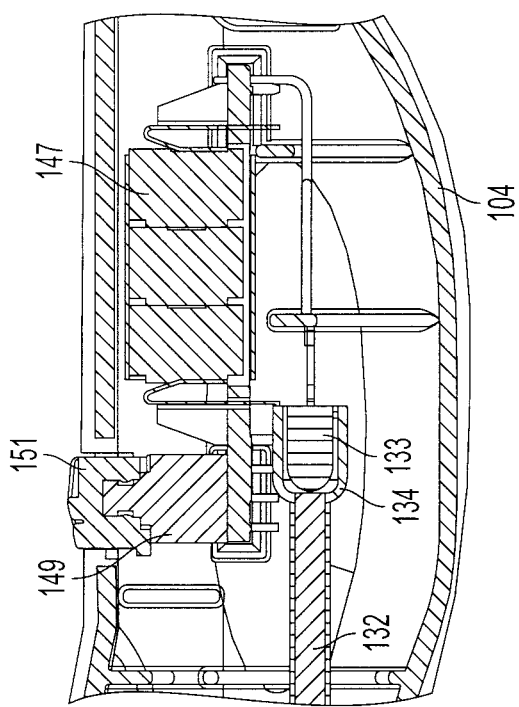
FIG. 15 is a close-up cross-sectional view of a handle portion of the device of FIG. 7 for the embodiment of the light assembly of FIG. 14.
Figure 14:
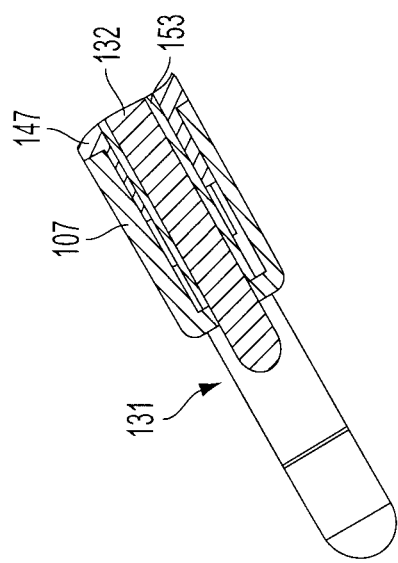
FIG. 14 is a close-up cross-sectional view of a tip portion of the device of FIG. 7 having another embodiment of the light assembly.

As shown in FIG. 14, in another alternative embodiments of device 30g, illuminator 131 may comprise an elongated flexible and cylindrical transparent fiber light guide 132, which preferably has a diameter of 1-2 mm and receives light from a light collector 134 which receives light from a light source, such as light emitting diode (LED) 133. As shown in FIG. 15, the light source is located in handle 104. In this manner, the light source and the wires 141, 141 may remain in handle 101 and not be provided as part of shaft assembly 101.

Light collector 134 collects light from the side lobes of LED 133 and focuses it into the light guide 132. The light collector/focuser 134 is designed to have an shape such that the light emitted by the LED 133 on reaching the collector's boundary is incidental to its surface under the angle which results in total internal reflection. In this manner, all light is forwarded toward the light guide 132 and a minimal amount of light escapes the light collector 134. The collector 132 is further shaped to focus the light exiting it into a beam which falls within the acceptance angle of the fiber, thus providing total reflection within the fiber. The indexes of refraction of the LED lens 135, the light collector 134 and the fiber light guide 132 are preferably selected to substantially be the same to minimize internal reflections in interfaces of these components. The lens at the distal end of the light guide 132 will control the geometry of the output light beam, and is preferably formed from the light guide 132 itself rather than a separate component.

Figure 16:
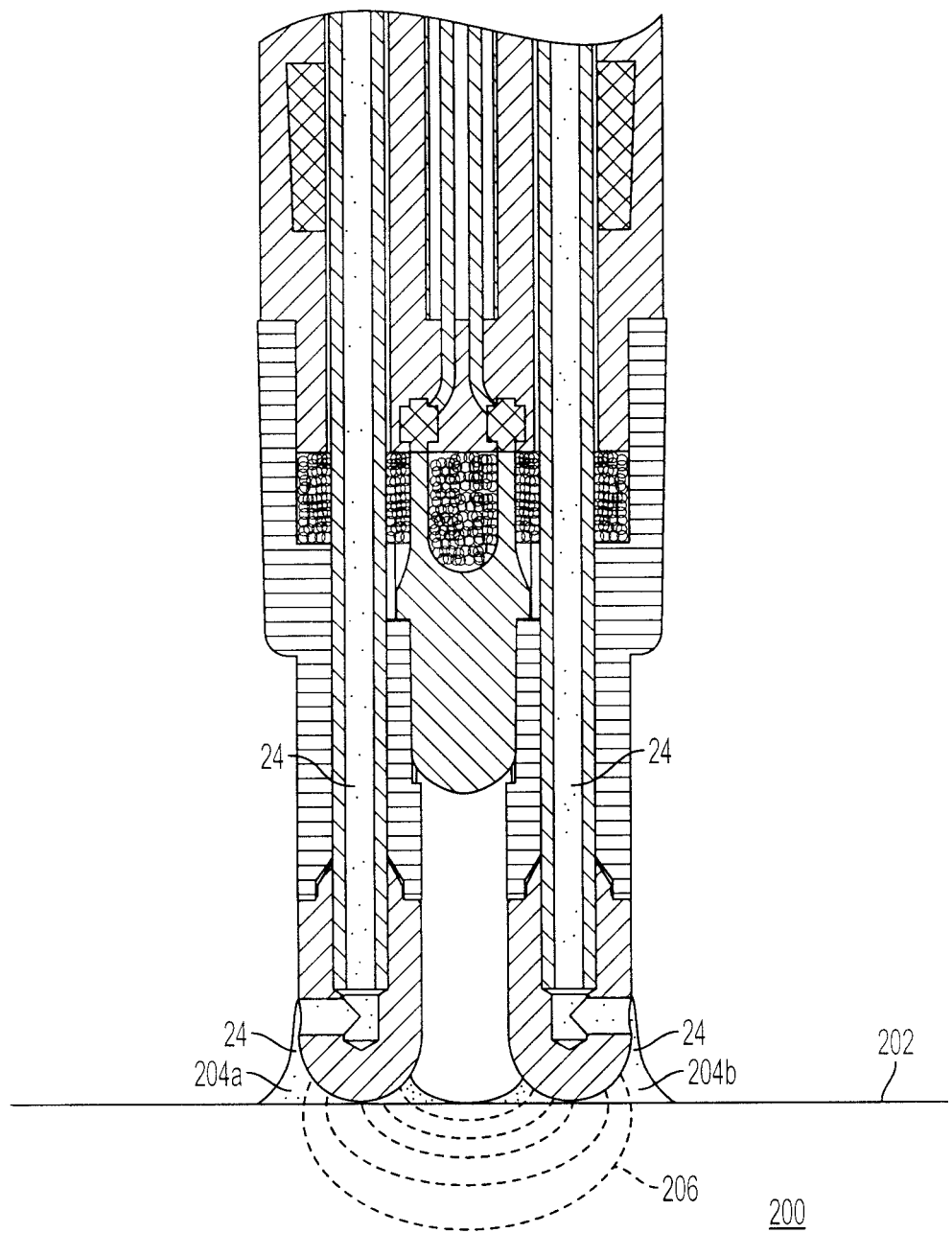
FIG. 16 is a close-up cross-sectional view of the tip portion of the device of FIG. 7 with an exemplary fluid coupling to a tissue surface of tissue.

As shown in FIG. 16, one way in which device 30g may be used is with the longitudinal axis of electrodes 114a, 114b vertically orientated, and the spherical surfaces 122a, 122b of electrodes 114a, 114b laterally spaced adjacent tissue surface 202 of tissue 200. Electrodes 114a, 114b are connected to electrosurgical unit 14 to provide RF power and form an alternating current electrical field in tissue 200 located between electrodes 114a and 114b. In the presence of alternating current, the electrodes 114a, 114b alternate polarity between positive and negative charges with current flow from the positive to negative charge. Without being bound to a particular theory, heating of the tissue is performed by electrical resistance heating.

Fluid 24, in addition to providing an electrical coupling between the device 30g and tissue 200, lubricates surface 202 of tissue 200 and facilitates the movement of electrodes 114a, 114b across surface 202 of tissue 200. During movement of electrodes 114a, 114b, electrodes 114a, 114b typically slide across the surface 202 of tissue 200. Typically the user of device 30e slides electrodes 114a, 114b across surface 202 of tissue 200 back and forth with a painting motion while using fluid 24 as, among other things, a lubricating coating. Preferably the thickness of the fluid 24 between the distal end surface of electrodes 114a, 114b and surface 202 of tissue 200 at the outer edge of couplings 204a, 204b is in the range between and including about 0.05 mm to 1.5 mm. Also, in certain embodiments, the distal end tip of electrodes 114a, 114b may contact surface 202 of tissue 200 without any fluid 24 in between.

As shown in FIG. 16, fluid couplings 204a, 204b comprise discrete, localized webs and more specifically comprise triangular shaped webs or bead portions providing a film of fluid 24 between surface 202 of tissue 200 and electrodes 114a, 114b. When the user of electrosurgical device 30g places electrodes 114a, 114b at a tissue treatment site and moves electrodes 114a, 114b across the surface 202 of the tissue 200, fluid 24 is expelled from fluid outlet openings 185a, 185b around and on surfaces 122a, 122b of electrodes 114a, 114b and onto the surface 202 of the tissue 200 via couplings 204a, 204b. At the same time, RF electrical energy, shown by electrical field lines 206, is provided to tissue 200 at tissue surface 202 and below tissue surface 202 into tissue 200 through fluid couplings 204a, 204b.

In order to better maintain fluid couplings 204a, 204b as separate couplings during use of device 30g, having a gap separation GS between electrodes 114a, 114b of at least about 2.0 mm in combination with the positioning of fluid outlets 185a, 185b has been found to inhibit undesirable merging of fluid couplings 204a, 204b.

As best shown in FIG. 16, the fluid outlet arrangement of device 30g expels fluid onto the electrodes 114a, 114b solely at locations remote from electrode surface portions facing each other. More particularly, fluid outlet opening 185a expels fluid onto electrode 114a at an electrode location remote from the surface portion of electrode 114a facing electrode 114b, and fluid outlet 185b expels fluid onto the electrode 114b at an electrode location remote from the surface portion of electrode 114b facing electrode 114a.

Figure 17:
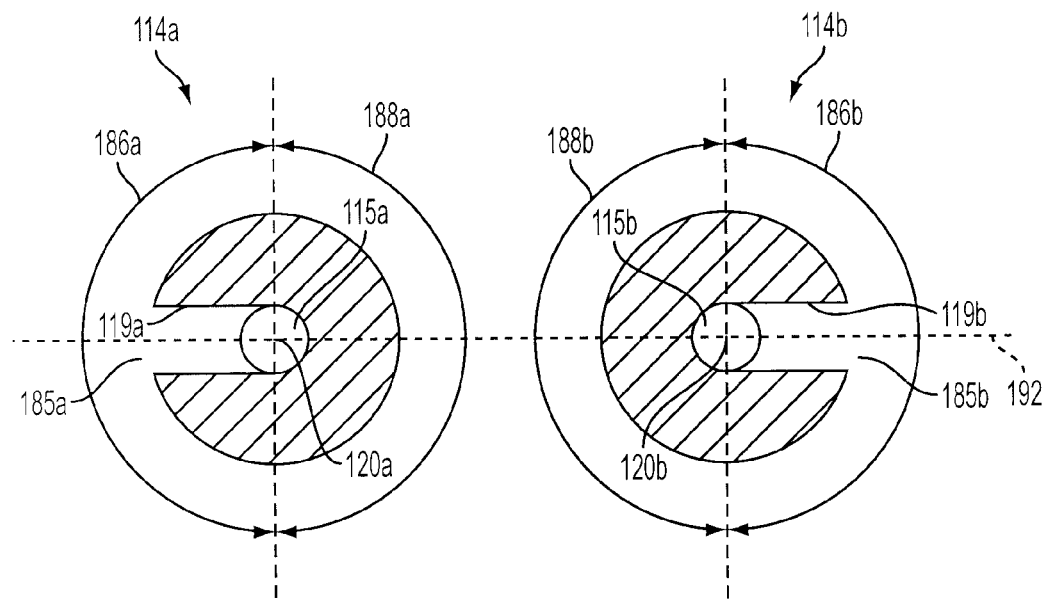
FIG. 17 is a close-up cross-sectional view of the tip portion of the device of FIG. 7 taken along line 17-17 of FIG. 7.

Even more particularly, fluid outlet opening 185a expels fluid onto a lateral surface portion 186a of electrode 114a, and fluid outlet opening 185b expels fluid onto a lateral surface portion 186b of electrode 114b. As shown in FIG. 17, the lateral surface portion 186a of electrode 114a comprises a semi-cylindrical surface portion of electrode 114a having a cylindrical arc of about 180 degrees, and the lateral surface portion 186b of electrode 114b is also provided by a semi-cylindrical surface portion of electrode 114b having a cylindrical arc of about 180 degrees.

Also as shown in FIG. 17, the surface portion of electrode 114a facing electrode 114b is provided by a medial surface portion 188a of electrode 114a, and the surface portion of electrode 114b facing electrode 114a is provided by a medial surface portion 188b of electrode 114b. As shown, the medial surface portion 188a of electrode 114a is provided by a semi-cylindrical surface portion of electrode 114a having a cylindrical arc of about 180 degrees, and the medial surface portion 188b of electrode 114b is also provided by a semi-cylindrical surface portion of electrode 114b having a cylindrical arc of about 180 degrees.

Figure 18:
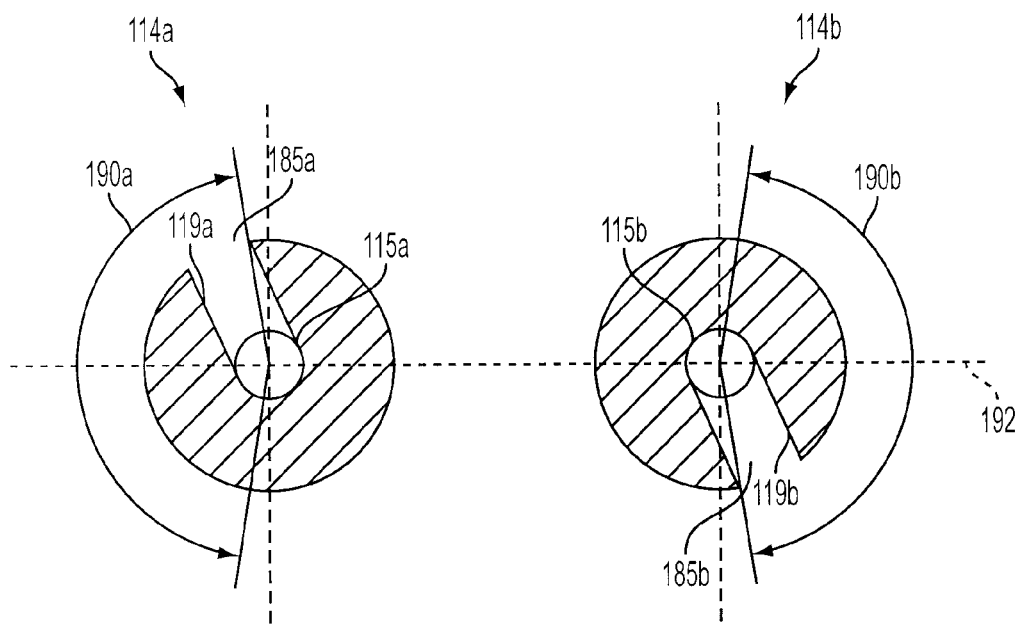
FIG. 18 is a close-up cross-sectional view of another embodiment of the tip portion of the device of FIG. 7 taken along line 17-17 of FIG. 7.

As shown in FIG. 18, a flat plane 192 passes through the longitudinal axis 120a of electrode 114a and the longitudinal axis 120b of electrode 114b. Fluid outlet opening 185a may be provided within a localized area 190a of the lateral surface portion 186a of electrode 114a which, as shown, comprises a cylindrical arc of about 150 degrees provided equally on each side of plane 192. Similarly, fluid outlet opening 185b may be provided within a localized area 190b of the lateral surface portion 186b of electrode 114b which, as shown, comprises a cylindrical arc of about 150 degrees provided equally on each side of plane 192. In other embodiments, the localized areas 190a, 190b of the lateral surface portions 186a, 186b may comprise narrower cylindrical arcs such as about 135, 120, 105, 90, 75, 60, 45 30 and 15 degrees provided equally on each side of plane 192. In still other embodiments, the localized areas 190a, 190b of the lateral surface portions 186a, 186b may comprise wider cylindrical arcs such as about 155, 160, 165, 170 and 175 degrees provided equally on each side of plane 192. As best shown in FIGS. 16 and 17, both fluid outlet opening 185a and fluid outlet opening 185b are provided on the plane 192, which desirably places the fluid outlet openings 185a, 185b at the most extreme lateral area of electrodes 114a, 114b, respectively.

The bipolar devices disclosed herein are particularly useful as non-coaptive tissue sealers in providing hemostasis during surgery. In other words, grasping of the tissue is not necessary to shrink, coagulate and seal tissue against blood loss, for example, by shrinking collagen and associated lumens of blood vessels (e.g., arteries, veins) to provided the desired hemostasis of the tissue. Furthermore, the control system of the electrosurgical unit 12 is not necessarily dependent on tissue feedback such as temperature or impedance to operate. Thus, the control system of electrosurgical unit 12 may be open loop with respect to the tissue which simplifies use.

Bipolar device 30g disclosed herein are particularly useful to surgeons to achieve hemostasis after dissecting through soft tissue, as part of hip or knee arthroplasty. The tissue treating portions can be painted over the raw, oozing surface 202 of tissue 200 to seal the tissue 200 against bleeding, or focused on individual larger bleeding vessels to stop vessel bleeding. As part of the same or different procedure, bipolar device 30g is also useful to stop bleeding from the surface of cut bone, or osseous, tissue as part of any orthopaedic procedure that requires bone to be cut. Device 30g may be particularly useful for use during orthopedic knee, hip, shoulder and spine procedures. Additional discussion concerning such procedures may be found in U.S. Publication No. 2006/0149225, published Jul. 6, 2006, and U.S. Publication No. 2005/0090816, published Apr. 28, 2005, which are assigned to the assignee of the present invention and are hereby incorporated by reference in there entirety to the extent they are consistent.

With regards to spine procedures, for example, where an intervertebral disc cannot be repaired and must be removed as part of a discectomy, device 30g may be particularly useful to seal and arrest bleeding from the cancellous bone of opposing upper and lower vertebra surfaces (e.g. the cephalad surface of the vertebral body of a superior vertebra and the caudad surface of an inferior vertebra). Device 30g may also be particularly useful to shrink blood vessels, either severed or unsevered, during such surgery, such as blood vessels of the vertebral venous and/or arterial systems.

Intervertebral discs are flexible pads of fibrocartilaginous tissue tightly fixed between the vertebrae of the spine. The discs comprise a flat, circular capsule roughly an inch in diameter and about 0.25 inch thick, made of a tough, fibrous outer membrane called the annulus fibrosus, surrounding an elastic core called the nucleus pulposus.

Under stress, it is possible for the nucleus pulposus to swell and herniate, pushing through a weak spot in the annulus fibrosus membrane of the disc and into the spinal canal. Consequently, all or part of the nucleus pulposus material may protrude through the weak spot, causing pressure against surrounding nerves which results in pain and immobility.

Where a damaged intervertebral disc must be removed from the patient as part of a discectomy and subsequent fusion of vertebral bodies of the superior and inferior vertebrae, the devices of the present invention may be particularly useful to shrink and seal blood vessels of the vertebral venous and/or arterial systems.

The vertebral venous system includes any of four interconnected venous networks surrounding the vertebral column. These are known as the anterior external vertebral venous plexus (the system around the vertebral bodies), the posterior external vertebral venous plexus (the system around the vertebral processes), the anterior internal vertebral (epidural) venous plexus (the system running the length of the vertebral canal anterior to the dura) and the posterior internal vertebral (epidural) venous plexus (the system running the length of the vertebral canal posterior to the dura), with the latter two constituting the epidural venous plexus. The veins of the exterior vertebral venous plexus communicate with the veins of the interior vertebral venous plexus through intervertebral veins and anterior and posterior segmental medullary/radicular veins of each vertebral level.

The vertebral arterial system includes the segmental arteries of the vertebral column which supply anterior and posterior radicular arteries of the various vertebral levels. In thoracic and lumbar regions, segmental arteries include the posterior intercostal, subcostal and lumbar arteries, which arise from posterior aspect of the aorta. The blood supply to the spinal column is derived from the segmental arteries, which supply two networks: one feeds the bony elements of the vertebrae, the paraspinal muscles, and the extradural space; and the other, an inner network, nourishes the spinal cord itself.

Extending from the aorta, the segmental arteries hug the perimeter of the vertebral bodies of the vertebrae, giving off paravertebral anastomoses, prevertebral anastomoses and a main dorsal branch as they approach the neural foramina. This main dorsal branch continues posteriorly below the transverse process of the vertabrae, supplying the bone of the posterior elements of the vertebrae and the paraspinal muscles. Shortly after its origin, the dorsal branch gives off a spinal branch, which supplies the anterior radicular artery and anterior segmental medullary artery, which ultimately supplies the anterior spinal artery. The spinal branch also supplies a branch to the vertebral body and dura mater, and the posterior radicular artery which ultimately supplies the posterior spinal arteries.

During a posterior discectomy, the devices of the present invention may be more particularly used by a surgeon to seal veins of the posterior external vertebral venous plexus, posterior internal vertebral (epidural) venous plexus and anterior internal vertebral (epidural) venous plexus prior to entering the intervertebral disc space. Alternatively, during an anterior discectomy, the devices of the present invention may be more particularly used by a surgeon to seal veins of the anterior external vertebral venous plexus and segmental arteries, particularly the anterior and lateral-anterior portions adjacent the vertebral bodies.

As established above, device 30g of the present invention inhibit such undesirable effects of tissue desiccation, electrode sticking, char formation and smoke generation, and thus do not suffer from the same drawbacks as prior art dry tip electrosurgical devices. The use of the disclosed devices can result in significantly lower blood loss during surgical procedures. Such a reduction in blood loss can reduce or eliminate the need for blood transfusions, and thus the cost and negative clinical consequences associated with blood transfusions, such as prolonged hospitalization.

While a preferred embodiment of the present invention has been described, it should be understood that various changes, adaptations and modifications can be made therein without departing from the spirit of the invention and the scope of the appended claims. The scope of the invention should, therefore, be determined not with reference to the above description, but instead should be determined with reference to the appended claims along with their full scope of equivalents. Furthermore, it should be understood that the appended claims do not necessarily comprise the broadest scope of the invention which the Applicant is entitled to claim, or the only manner(s) in which the invention may be claimed, or that all recited features are necessary.

All publications and patent documents cited in this application are incorporated by reference in their entirety for all purposes to the extent they are consistent.

What is claimed:

1. A fluid-assisted bipolar electrosurgical device to treat tissue in a presence of radio frequency energy and a fluid provided from the device, the device comprising:
   a malleable shaft assembly comprising a first shaft and a second shaft, a length of the first shaft and a length of the second shaft encapsulated in an outer member comprising a polymer, and at least a portion of the first shaft and at least a portion of the second shaft being malleable to be manually shapeable by a user of the device;
   a first electrode and a second electrode projecting from an end of the malleable shaft assembly;
   at least one fluid outlet to deliver the fluid to the tissue,
   the first electrode is retained at a distal end of the first shaft;
   the second electrode is retained at a distal end of the second shaft;
   the first electrode is laterally spaced from the second electrode a predetermined distance;
   the outer member being configured to retain the first electrode and the second electrode stationary relative to each other at a predetermined orientation and lateral separation distance even if the shaft assembly is bent,
   wherein the first electrode and the second electrode are configured to slide across the tissue surface in the presence of the radio frequency energy and the fluid.

2. The device of claim 1 wherein:
   the outer member comprises a single member surrounding both the first shaft and the second shaft.

3. The device of claim 1 wherein:
   the malleable portion of the first shaft is the length of the first shaft disposed in the outer member, and
   the malleable portion of the second shaft is the length of the second shaft disposed in the outer member.

4. The device of claim 1 wherein:
   the polymer comprises a thermoplastic polymer.

5. The device of claim 1 wherein:
   the polymer comprises an elastomer.

6. The device of claim 1 wherein:
   at least one of the first shaft and the second shaft comprises metal.

7. The device of claim 1 wherein:
   at least a portion of the first shaft is parallel with at least a portion of the second shaft.

8. The device of claim 1 wherein:
   the first electrode and the second electrode are of substantially a same size.

9. The device of claim 1 wherein:
   the first electrode comprises a domed shape; and
   the second electrode comprises a domed shape.

10. The device of claim 1 wherein:
    the first electrode comprises a spherical distal end; and
    the second electrode comprises a spherical distal end.

11. The device of claim 1 wherein:
    the at least one fluid outlet further comprises at least one fluid outlet to provide fluid to the first electrode and at least one fluid outlet to provide fluid to the second electrode.

12. The device of claim 11 wherein:
    the at least one fluid outlet to provide fluid to the first electrode is defined entirely by the first electrode; and
    the at least one fluid outlet to provide fluid to the second electrode is defined entirely by the second electrode.

13. The device of claim 11 wherein:
    the first electrode is disposed adjacent to the second electrode;
    the first electrode defines a single fluid outlet disposed on a side of the first electrode opposite the second electrode; and
    the second electrode defines a single fluid outlet disposed on a side of the second electrode opposite the first electrode.

14. The device of claim 11 wherein:
    the first electrode defines a first longitudinally-oriented bore and a first transversely-oriented bore intersecting the first longitudinally-oriented bore;
    the second electrode defines a second longitudinally-oriented bore and a second transversely-oriented bore intersecting the second longitudinally-oriented bore;
    the at least one fluid outlet to provide fluid to the first electrode is at least partially defined by the first transversely-oriented bore; and
    the at least one fluid outlet to provide fluid to the second electrode is at least partially defined by the second transversely-oriented bore.

15. The device of claim 11 wherein:
    the first electrode is laterally spaced from the second electrode;
    the at least one fluid outlet to provide fluid to the first electrode further releases the fluid through a bore only at a lateral side of the first electrode; and
    the at least one fluid outlet to provide fluid to the second electrode further releases the fluid through a bore only at a lateral side of the second electrode.

16. The device of claim 11 further comprising:
    a first fluid delivery passage in fluid communication with the at least one fluid outlet to provide fluid to the first electrode; and
    a second fluid delivery passage in fluid communication with the at least one fluid outlet to provide fluid to the second electrode.

17. A fluid-assisted bipolar electrosurgical device to treat tissue in a presence of radio frequency energy and a fluid provided from the device, the device comprising:
    a malleable shaft assembly comprising a first shaft and a second shaft, a length of the first shaft and a length of the second shaft encapsulated in an outer member comprising a polymer, and at least a portion of the first shaft and at least a portion of the second shaft being malleable to be manually shapeable by a user of the device;
    a first electrode and a second electrode projecting from an end of the malleable shaft assembly;
    at least one fluid outlet to deliver the fluid to the tissue,
    the first electrode is retained at a distal end of the first shaft;
    the second electrode is retained at a distal end of the second shaft, the first electrode is laterally spaced from the second electrode a predetermined distance;
the outer member being configured to retain the first electrode and the second electrode stationary relative to each other at a predetermined orientation and lateral separation distance even if the shaft assembly is bent,
wherein the first electrode and the second electrode are configured to slide across the tissue surface in the presence of the radio frequency energy and the fluid; and
a lighting assembly.

18. The device of claim 17 wherein:
the lighting assembly comprises an illuminator, and
the illuminator is configured to direct illumination towards the first electrode and the second electrode.

19. The device of claim 18 wherein:
the illuminator is disposed between a distal portion of the first shaft and a distal portion of the second shaft.

20. The device of claim 18 wherein:
the illuminator is disposed adjacent the first electrode and the second electrode.

21. The device of claim 18 wherein:
the illuminator is located in a housing at the end of the malleable shaft assembly, and
the housing is at least one of translucent and transparent.

22. The device of claim 18 wherein:
the illuminator comprises a light source.

23. The device of claim 22 wherein:
the light source comprises a light emitting diode.

24. The device of claim 18 wherein:
the illuminator comprises an elongated transparent light guide.

25. A fluid-assisted bipolar electrosurgical device to treat tissue in a presence of radio frequency energy and a fluid provided from the device, the device comprising:
a malleable shaft assembly comprising a first shaft and a second shaft, a length of the first shaft and a length of the second shaft encapsulated in an outer member comprising a polymer, and at least a portion of the first shaft and at least a portion of the second shaft being malleable to be manually shapeable by a user of the device;
a first electrode and a second electrode projecting from an end of the malleable shaft assembly;
at least one fluid outlet to deliver the fluid to the tissue,
a first electrode is retained at a distal end of the first shaft;
a second electrode is retained at a distal end of the second shaft,
a first electrode is laterally spaced from the second electrode a predetermined distance;
the outer member being configured to retain the first electrode and the second electrode stationary relative to each other at a predetermined orientation and lateral separation distance even if the shaft assembly is bent,
wherein the first electrode and the second electrode are configured to slide across the tissue surface in the presence of the radio frequency energy and the fluid;
a lighting assembly; and
the lighting assembly comprises a light source and a power source in a handle of the device.

26. The device of claim 1, further comprising:
a light source disposed at a distal portion of the malleable shaft assembly;
a tube extending longitudinally within the malleable shaft assembly; and
wires coupled to the light source, extending within the tube, wherein the outer member surrounds the tube.

27. The device of claim 1, wherein:
the first shaft and the second shaft have variable stiffness along their lengths, and the malleable portions of the first and second shafts include only distal portions of the first and second shafts.

28. The device of claim 16, wherein:
the first fluid delivery passage is formed of a first fluid delivery shaft, wherein at least a portion of the first fluid shaft is located within a proximal end of a first electrode; and
the second fluid delivery passage is formed of a second fluid delivery shaft, wherein at least a portion of the second fluid shaft is located within a proximal end of the second electrode.

* * * * *